US007687459B2

(12) United States Patent
Niu et al.

(10) Patent No.: US 7,687,459 B2
(45) Date of Patent: Mar. 30, 2010

(54) ARYLALKOXYL HEPATITIS C VIRUS PROTEASE INHIBITORS

(75) Inventors: Deqiang Niu, Lexington, MA (US); Yonghua Gai, North Grafton, MA (US); Yat Sun Or, Watertown, MA (US); Zhe Wang, Hockessin, DE (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 101 days.

(21) Appl. No.: 11/836,288

(22) Filed: Aug. 9, 2007

(65) Prior Publication Data
US 2009/0041721 A1 Feb. 12, 2009

Related U.S. Application Data

(60) Provisional application No. 61/007,901, filed on Aug. 11, 2006.

(51) Int. Cl.
A61K 38/12 (2006.01)
A61K 38/06 (2006.01)
A61K 39/42 (2006.01)

(52) U.S. Cl. .......................... 514/11; 514/18; 530/317; 530/330; 424/149.1

(58) Field of Classification Search ....................... None
See application file for complete search history.

(56) References Cited

U.S. PATENT DOCUMENTS

| 6,323,180 | B1 | 11/2001 | Linas-Brunet et al. | |
|---|---|---|---|---|
| 6,608,027 | B1 | 8/2003 | Tsantrizos et al. | |
| 6,867,185 | B2 | 3/2005 | Campbell et al. | |
| 6,995,174 | B2 | 2/2006 | Wang et al. | |
| 7,132,504 | B2 | 11/2006 | Scola et al. | |
| 7,135,462 | B2 | 11/2006 | Scola et al. | |
| 7,173,004 | B2 | 2/2007 | McPhee et al. | |
| 7,176,208 | B2 | 2/2007 | Nakajima et. al. | |
| 7,273,851 | B2 | 9/2007 | Miao et al. | |
| 2004/0106559 | A1* | 6/2004 | Wang et al. ................... | 514/18 |
| 2005/0137139 | A1 | 6/2005 | Perni et al. | |
| 2005/0153877 | A1 | 7/2005 | Miao | |
| 2005/0267018 | A1* | 12/2005 | Blatt et al. .................... | 514/9 |
| 2006/0122123 | A1 | 6/2006 | Chaudhary et al. | |
| 2006/0172950 | A1 | 8/2006 | Wang et al. | |
| 2007/0099825 | A1 | 5/2007 | D'Andrea et al. | |

FOREIGN PATENT DOCUMENTS

WO 0009543 2/2000
WO 2005/010029 A1 2/2005

OTHER PUBLICATIONS

H.-K. Han. AAPS Pharmsci. (2000) 2(1), pp. 1-11.*
P. Ettmayer et al. J. Med. Chem. (2004) 47(10).*
B. Testa. Biochem. Pharm. (2004) 68, pp. 2097-2106.*
Llinas-Brunet, et. al., Bioorganic & Medicinal Chemistry Letters, 8, 1998, 1713-1718.
Griffith et. al., Annual Reports in Medicianl Chemistry, 39, 2004, 223-237.
Wangsell, F., Design and Synthesis of Serine and Aspartic Protease Inhibitors, Linkopig Studies and Technology, Thesis No. 1264, 2006.
Tsantrizos, et al., "Macrocyclic Inhibitors of the NS3 Protease as Potential Therapeutic Agents of Hepatitis C Virus Infection," Angew. Chem. Int. Ed. 2003, 42, No. 12, 1355-1360.

* cited by examiner

Primary Examiner—Andrew D Kosar
Assistant Examiner—Satyanarayana R Gudibande
(74) Attorney, Agent, or Firm—Carolyn S. Elmore; Edgar W. Harlan; Elmore Patent Law Group P.C.

(57) ABSTRACT

The present invention discloses compounds of Formula I or II, or pharmaceutically acceptable salts, esters, or prodrugs thereof:

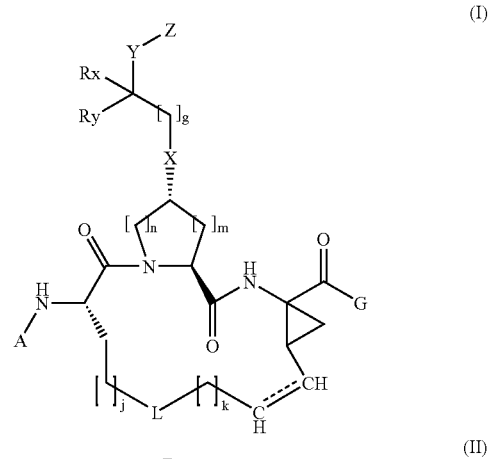

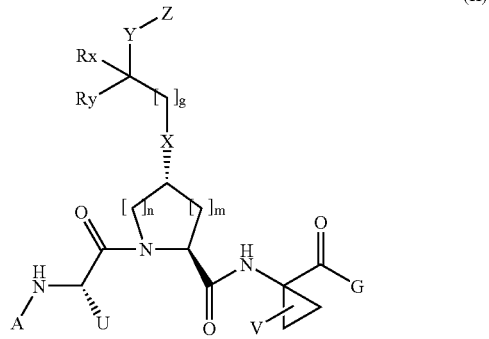

which inhibit serine protease activity, particularly the activity of hepatitis C virus (HCV) NS3-NS4A protease. Consequently, the compounds of the present invention interfere with the life cycle of the hepatitis C virus and are also useful as antiviral agents. The present invention further relates to pharmaceutical compositions comprising the aforementioned compounds for administration to a subject suffering from HCV infection. The invention also relates to methods of treating an HCV infection in a subject by administering to the subject a pharmaceutical composition comprising a compound of the present invention.

18 Claims, No Drawings

SEQUENCE LISTING

<160> NUMBER OF SEQ ID NOS: 3

<210> SEQ ID NO 1
<211> LENGTH: 18
<212> TYPE: DNA
<213> ORGANISM: Artificial Sequence
<220> FEATURE:
<223> OTHER INFORMATION: Forward Primer

<400> SEQUENCE: 1
gctgcggcct gtcgagct                                                 18

<210> SEQ ID NO 2
<211> LENGTH: 19
<212> TYPE: DNA
<213> ORGANISM: Artificial Sequence
<220> FEATURE:
<223> OTHER INFORMATION: Reverse Primer

<400> SEQUENCE: 2
caaggtcgtc tccgcatac                                                19

```
<210> SEQ ID NO 3
<211> LENGTH: 25
<212> TYPE: DNA
<213> ORGANISM: Artificial Sequence
<220> FEATURE:
<223> OTHER INFORMATION: Probe

<400> SEQUENCE: 3
cgaagctcca ggactgcacg atgct                                    25
```

ARYLALKOXYL HEPATITIS C VIRUS PROTEASE INHIBITORS

CROSS-REFERENCE TO RELATED APPLICATIONS

This application claims benefit of U.S. provisional application 61/007,901 (conversion of U.S. application Ser. No. 11/503,413) filed Aug. 11, 2006, the entire content of which is herein incorporated by reference.

TECHNICAL FIELD

The present invention relates to arylalkoxyl hepatitis C virus (HCV) protease inhibitors having antiviral activity against HCV and useful in the treatment of HCV infections. More particularly, the invention relates to arylalkoxyl HCV protease inhibitors, compositions containing such compounds and methods for using the same, as well as processes for making such compounds.

BACKGROUND OF THE INVENTION

HCV is the principal cause of non-A, non-B hepatitis and is an increasingly severe public health problem both in the developed and developing world. It is estimated that the virus infects over 200 million people worldwide, surpassing the number of individuals infected with the human immunodeficiency virus (HIV) by nearly five fold. HCV infected patients, due to the high percentage of individuals inflicted with chronic infections, are at an elevated risk of developing cirrhosis of the liver, subsequent hepatocellular carcinoma and terminal liver disease. HCV is the most prevalent cause of hepatocellular cancer and cause of patients requiring liver transplantation in the western world.

There are considerable barriers to the development of anti-HCV therapeutics, which include, but are not limited to, the persistence of the virus, the genetic diversity of the virus during replication in the host, the high incident rate of the virus developing drug-resistant mutants, and the lack of reproducible infectious culture systems and small-animal models for HCV replication and pathogenesis. In a majority of cases, given the mild course of the infection and the complex biology of the liver, careful consideration must be given to antiviral drugs, which are likely to have significant side effects.

Only two approved therapies for HCV infection are currently available. The original treatment regimen generally involves a 3-12 month course of intravenous interferon-alpha (IFN-α), while a new approved second-generation treatment involves co-treatment with IFN-α and the general antiviral nucleoside mimics like ribavirin. Both of these treatments suffer from interferon-related side effects as well as low efficacy against HCV infections. There exists a need for the development of effective antiviral agents for treatment of HCV infection due to the poor tolerability and disappointing efficacy of existing therapies.

In a patient population where the majority of individuals are chronically infected and asymptomatic and the prognoses are unknown, an effective drug preferably possesses significantly fewer side effects than the currently available treatments. The hepatitis C non-structural protein-3 (NS3) is a proteolytic enzyme required for processing of the viral polyprotein and consequently viral replication. Despite the huge number of viral variants associated with HCV infection, the active site of the NS3 protease remains highly conserved thus making its inhibition an attractive mode of intervention. Recent success in the treatment of HIV with protease inhibitors supports the concept that the inhibition of NS3 is a key target in the battle against HCV.

HCV is a flaviridae type RNA virus. The HCV genome is enveloped and contains a single strand RNA molecule composed of circa 9600 base pairs. It encodes a polypeptide comprised of approximately 3010 amino acids.

The HCV polyprotein is processed by viral and host peptidase into 10 discreet peptides which serve a variety of functions. There are three structural proteins, C, E1 and E2. The P7 protein is of unknown function and is comprised of a highly variable sequence. There are six non-structural proteins. NS2 is a zinc-dependent metalloproteinase that functions in conjunction with a portion of the NS3 protein. NS3 incorporates two catalytic functions (separate from its association with NS2): a serine protease at the N-terminal end, which requires NS4A as a cofactor, and an ATP-ase-dependent helicase function at the carboxyl terminus. NS4A is a tightly associated but non-covalent cofactor of the serine protease.

The NS3-NS4A protease is responsible for cleaving four sites on the viral polyprotein. The NS3-NS4A cleavage is autocatalytic, occurring in cis. The remaining three hydrolyses, NS4A-NS4B, NS4B-NS5A and NS5A-NS5B all occur in trans. NS3 is a serine protease which is structurally classified as a chymotrypsin-like protease. While the NS serine protease possesses proteolytic activity by itself, the HCV protease enzyme is not an efficient enzyme in terms of catalyzing polyprotein cleavage. It has been shown that a central hydrophobic region of the NS4A protein is required for this enhancement. The complex formation of the NS3 protein with NS4A seems necessary to the processing events, enhancing the proteolytic efficacy at all of the sites.

A general strategy for the development of antiviral agents is to inactivate virally encoded enzymes, including NS3, that are essential for the replication of the virus. Current efforts directed toward the discovery of NS3 protease inhibitors were reviewed by S. Tan, A. Pause, Y. Shi, N. Sonenberg, Hepatitis C Therapeutics: Current Status and Emerging Strategies, Nature Rev. Drug Discov., 1, 867-881 (2002).

SUMMARY OF THE INVENTION

The present invention relates to arylalkoxyl HCV protease inhibitors including pharmaceutically acceptable salts, esters, or prodrugs thereof which inhibit serine protease activity, particularly the activity of hepatitis C virus (HCV) NS3-NS4A protease. Consequently, the infection in a subject in need of such therapy with said macrocyclic compounds of the present invention interfere with the life cycle of the hepatitis C virus and are also useful as antiviral agents. The present invention further relates to pharmaceutical compositions comprising the aforementioned compounds, salts, esters or prodrugs for administration to a subject suffering from HCV infection. The present invention further features pharmaceutical compositions comprising a compound of the present invention (or a pharmaceutically acceptable salt, ester or prodrug thereof) and another anti-HCV agent, such interferon (e.g., alpha-interferon, beta-interferon, consensus interferon, pegylated interferon, or albumin or other conjugated interferon), ribavirin, amantadine, another HCV protease inhibitor, or an HCV polymerase, helicase or internal ribosome entry site inhibitor. The invention also relates to methods of treating an HCV infection in a subject by administering a pharmaceutical composition of the present invention.

In one embodiment of the present invention there are disclosed compounds represented by Formula I or II, or pharmaceutically acceptable salts, esters, or prodrugs thereof:

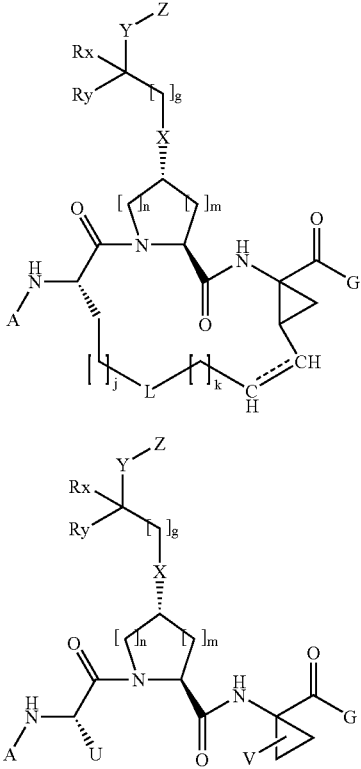

(I)

(II)

wherein

A is selected from H, —(C═O)—O—$R_1$, —(C═O)—$R_2$, —C(═O)—NH—$R_2$, and —S(O)$_2$—$R_1$, —S(O)$_2$NH$R_2$;

each $R_1$ is independently selected from the group consisting of:
(i) aryl;
(ii) substituted aryl;
(iii) heteroaryl;
(iv) substituted heteroaryl;
(v) Heterocycloalkyl;
(vi) substituted heterocycloalkyl;
(vii) —$C_1$-$C_8$ alkyl, —$C_2$-$C_8$ alkenyl, —$C_2$-$C_8$ alkynyl each containing 0, 1, 2, or 3 heteroatoms selected from O, S, or N;
(viii) substituted —$C_1$-$C_8$ alkyl, substituted —$C_2$-$C_8$ alkenyl, substituted —$C_2$-$C_8$ alkynyl each containing 0, 1, 2, or 3 heteroatoms selected from O, S or N;
(ix) —$C_3$-$C_{12}$ cycloalkyl;
(x) substituted —$C_3$-$C_{12}$ cycloalkyl;
(xi) —$C_3$-$C_{12}$ cycloalkenyl; and
(xii) substituted —$C_3$-$C_{12}$ cycloalkenyl;

each $R_2$ is independently selected from the group consisting of:
(i) hydrogen;
(ii) aryl;
(iii) substituted aryl;
(iv) heteroaryl;
(v) substituted heteroaryl;
(vi) heterocycloalkyl;
(vii) substituted heterocycloalkyl;
(viii) —$C_1$-$C_8$ alkyl, —$C_2$-$C_8$ alkenyl, —$C_2$-$C_8$ alkynyl each containing 0, 1, 2, or 3 heteroatoms selected from O, S, or N;
(ix) substituted —$C_1$-$C_8$ alkyl, substituted —$C_2$-$C_8$ alkenyl, substituted —$C_2$-$C_8$ alkynyl each containing 0, 1, 2, or 3 heteroatoms selected from O, S or N;
(x) —$C_3$-$C_{12}$ cycloalkyl; or
(xi) substituted —$C_3$-$C_{12}$ cycloalkyl;
(xii) —$C_3$-$C_{12}$ cycloalkenyl; and
(xiii) substituted —$C_3$-$C_{12}$ cycloalkenyl;

G is selected from —OH, —NHS(O)$_2$—$R_3$, —NH(SO$_2$)N$R_4R_5$;

each $R_3$ is independently selected from:
(i) aryl;
(ii) substituted aryl;
(iii) heteroaryl;
(iv) substituted heteroaryl;
(v) heterocycloalkyl;
(vi) substituted heterocycloalkyl;
(vii) —$C_1$-$C_8$ alkyl, —$C_2$-$C_8$ alkenyl, —$C_2$-$C_8$ alkynyl each containing 0, 1, 2, or 3 heteroatoms selected from O, S or N;
(viii) substituted —$C_1$-$C_8$ alkyl, substituted —$C_2$-$C_8$ alkenyl, substituted —$C_2$-$C_8$ alkynyl each containing 0, 1, 2, or 3 heteroatoms selected from O, S or N;
(ix) —$C_3$-$C_{12}$ cycloalkyl;
(x) substituted —$C_3$-$C_{12}$ cycloalkyl;
(xi) —$C_3$-$C_{12}$ cycloalkenyl; and
(xii) substituted —$C_3$-$C_{12}$ cycloalkenyl;

each $R_4$ and $R_5$ are independently selected from:
(i) hydrogen;
(ii) aryl;
(iii) substituted aryl;
(iv) heteroaryl;
(v) substituted heteroaryl;
(vi) heterocycloalkyl;
(vii) substituted heterocycloalkyl;
(viii) —$C_1$-$C_8$ alkyl, —$C_2$-$C_8$ alkenyl, —$C_2$-$C_8$ alkynyl each containing 0, 1, 2, or 3 heteroatoms selected from O, S, or N;
(ix) substituted —$C_1$-$C_8$ alkyl, substituted —$C_2$-$C_8$ alkenyl, substituted —$C_2$-$C_8$ alkynyl each containing 0, 1, 2, or 3 heteroatoms selected from O, S or N;
(x) —$C_3$-$C_{12}$ cycloalkyl;
(xi) substituted —$C_3$-$C_{12}$ cycloalkyl;
(xii) —$C_3$-$C_{12}$ cycloalkenyl; and
(xiii) substituted —$C_3$-$C_{12}$ cycloalkenyl;

L is selected from —CH$_2$—, —O—, —S—, —S(O)$_2$—, —CO—, —C(O)O—, —C(O)NH—, —CHF— —CF$_2$—, aryl, substituted aryl, heteroaryl, and substituted heteroaryl;

U and V are independently selected from the group consisting of:
(i) hydrogen;
(ii) aryl; substituted aryl;
(iii) heteroaryl;
(iv) substituted heteroaryl;
(v) heterocyclic;
(vi) substituted heterocyclic;
(vii) —$C_1$-$C_8$ alkyl, —$C_2$-$C_8$ alkenyl, —$C_2$-$C_8$ alkynyl; each containing 0, 1, 2, or 3 heteroatoms selected from O, S or N;
(viii) substituted —$C_1$-$C_8$ alkyl, substituted —$C_2$-$C_8$ alkenyl, substituted —$C_2$-$C_8$ alkynyl each containing 0, 1, 2, or 3 heteroatoms selected from O, S or N;
(ix) —$C_3$-$C_{12}$ cycloalkyl;
(x) substituted —$C_3$-$C_{12}$ cycloalkyl;
(xi) —$C_3$-$C_{12}$ cycloalkenyl; and (xii) substituted —$C_3$-$C_{12}$ cycloalkenyl;
X is selected from the group consisting of:
(i) oxygen;
(ii) sulfur;
(iii) $NR_4$; where $R_4$ is as previously defined above;
Y is absent or is selected from the group consisting of:
(i) —$C_1$-$C_6$ alkyl containing 0, 1, 2, or 3 heteroatoms selected from O, S, or N, optionally substituted with one or more substituents selected from halogen, aryl, substituted aryl, heteroaryl, and substituted heteroaryl;
(ii) —$C_2$-$C_6$ alkenyl containing 0, 1, 2, or 3 heteroatoms selected from O, S, or N, optionally substituted with one or more substituents selected from halogen, aryl, substituted aryl, heteroaryl, and substituted heteroaryl;
(iii) —$C_2$-$C_6$ alkynyl containing 0, 1, 2, or 3 heteroatoms selected from O, S, or N, optionally substituted with one or more substituents selected from halogen, aryl, substituted aryl, heteroaryl, and substituted heteroaryl;
(iv) —$C_3$-$C_{12}$ cycloalkyl;
(v) substituted —$C_3$-$C_{12}$ cycloalkyl;
(vi) heterocycloalkyl; and
(vii) substituted heterocycloalkyl;
Z is selected from aryl, substituted aryl, heteroaryl, substituted heteroaryl;
Rx and Ry are each independently selected from a group consisting of:
(i) hydrogen;
(ii) aryl;
(iii) substituted aryl;
(iv) heteroaryl;
(v) substituted heteroaryl;
(vi) heterocycloalkyl;
(vii) substituted heterocycloalkyl;
(viii) —$C_1$-$C_8$ alkyl, —$C_2$-$C_8$ alkenyl, —$C_2$-$C_8$ alkynyl each containing 0, 1, 2, or 3 heteroatoms selected from O, S, or N;
(ix) substituted —$C_1$-$C_8$ alkyl, substituted —$C_2$-$C_8$ alkenyl, substituted —$C_2$-$C_8$ alkynyl each containing 0, 1, 2, or 3 heteroatoms selected from O, S or N;
(x) —$C_3$-$C_{12}$ cycloalkyl;
(xi) substituted —$C_3$-$C_{12}$ cycloalkyl;
(xii) —$C_3$-$C_{12}$ cycloalkenyl; and
(xiii) substituted —$C_3$-$C_{12}$ cycloalkenyl;
alternatively, when Rx is not hydrogen and Y is not absent, Rx can form a ring structure with W and Y, as shown in formula III or IV:

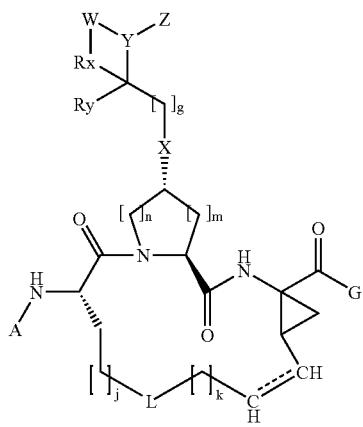

(III)

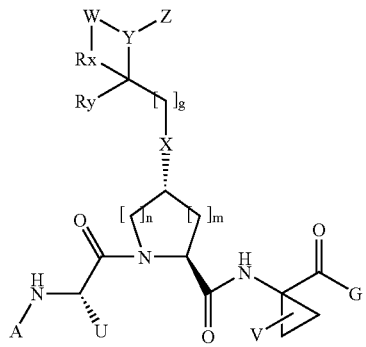

(IV)

wherein W is selected from $CH_2$, O, S, $NR_4R_5$, CO, $CH_2CH_2$, C(O)NH, $CH_2O$, $CH_2S$, and $CH_2NR_4$;

alternatively, when Rx is not hydrogen and Y is not absent, Rx can form a ring structure with W, Z, and Y as shown in formula V or VI:

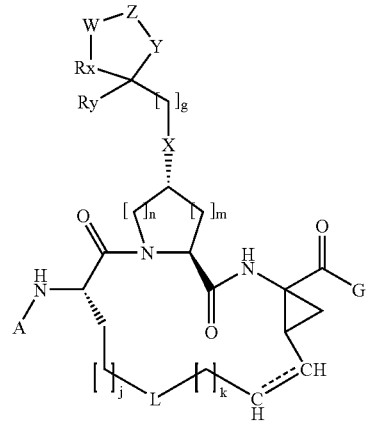

(V)

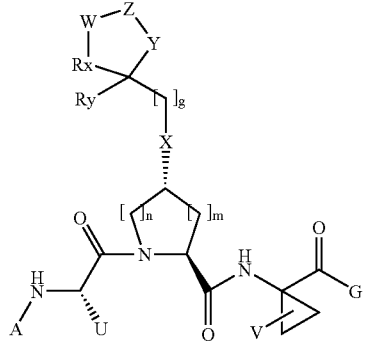

(VI)

g=0, 1, 2;
j=0, 1, 2, 3, or 4;
k=1, 2, or 3;
m=0, 1, or 2;
n=1, or 2; and
----- denotes a carbon-carbon single or double bond.

DETAILED DESCRIPTION OF THE INVENTION

A first embodiment of the invention is a compound represented by Formula I as described above, or a pharmaceutically acceptable salt, ester or prodrug thereof, alone or in combination with a pharmaceutically acceptable carrier or excipient.

A second embodiment of the invention is a compound represented by Formula II as described herein, or a pharmaceutically acceptable salt, ester or prodrug thereof, alone or in combination with a pharmaceutically acceptable carrier or excipient.

Certain aspects of the invention include, but are not limited to:

A compound of Formula VII or VIII:

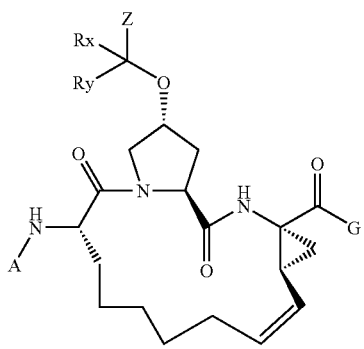
(VII)

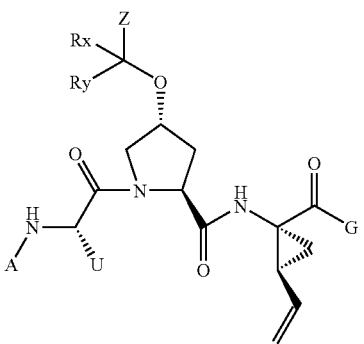
(VIII)

where A, G, Rx, Ry and Z are as defined in Formula I.

A compound of Formula IX or X:

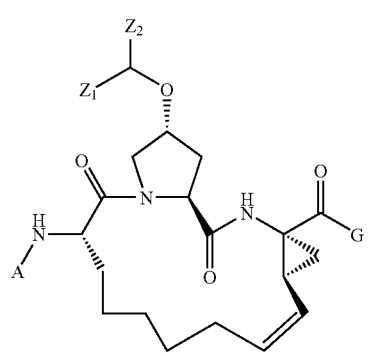
(IX)

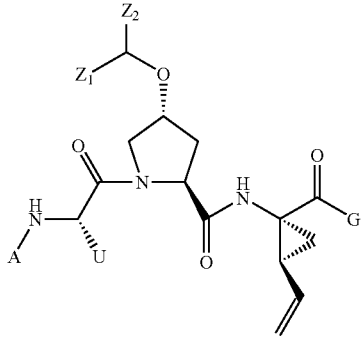
(X)

wherein each $Z_1$ and $Z_2$ is independently selected from aryl, substituted aryl, heteroaryl, and substituted heteroaryl; wherein A, G and U are as defined in Formula I.

A compound of Formula XI or XII:

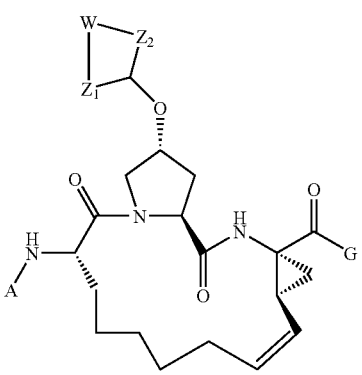
(XI)

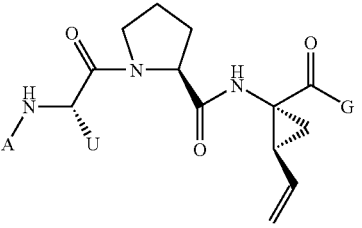
(XII)

wherein each $Z_1$ and $Z_2$ is independently selected from aryl, substituted aryl, heteroaryl, and substituted heteroaryl; W is selected from $CH_2$, O, S, $NR_4R_5$, CO, $CH_2CH_2$, C(O)NH, $CH_2O$, $CH_2S$, $CH_2NR_4$; and wherein $R_4$, $R_5$, A, G and U are as defined in Formula I.

A compound of Formula XIII or XIV:

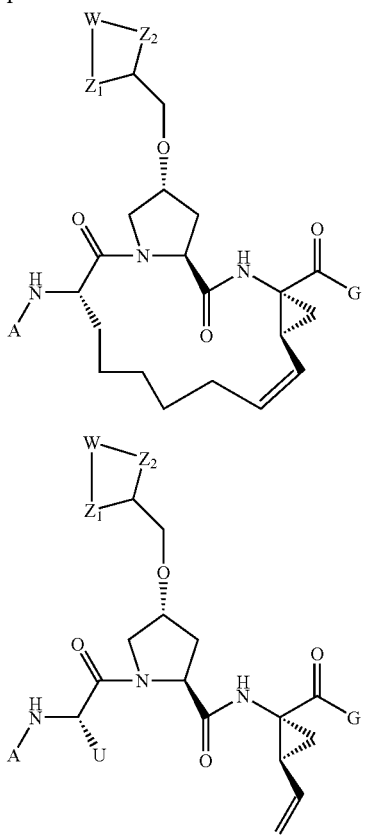

wherein each $Z_1$ and $Z_2$ is independently selected from aryl, substituted aryl, heteroaryl, and substituted heteroaryl; W is selected from $CH_2$, O, S, $NR_4R_5$, CO, $CH_2CH_2$, C(O)NH, $CH_2O$, $CH_2S$, $CH_2NR_4$; and wherein $R_4$, $R_5$, A, G and U are as defined in Formula I.

Representative compounds of the invention include, but are not limited to, the compounds 2-40 of the Formula XV:

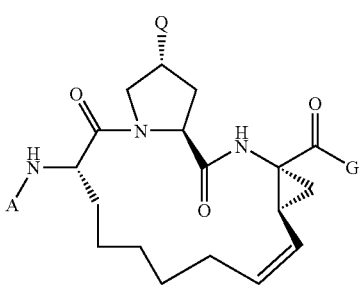

wherein A, Q and G are delineated for each example in Table 1.

TABLE 1

| Example # | A | Q | G |
|---|---|---|---|
| 2 | *tert*-butyl ester group | 8-quinolinylmethoxy | —OH |
| 3 | *tert*-butyl ester group | 2-biphenylmethoxy | —OH |
| 4 | *tert*-butyl ester group | 2-naphthylmethoxy | —OH |

TABLE 1-continued

| Example # | A | Q | G |
|---|---|---|---|
| 5 | tert-butyl 2-methylpropanoate group | 4-biphenylylmethoxy group | —OH |
| 6 | tert-butyl 2-methylpropanoate group | (3-bromobenzyl)oxy group | —OH |
| 7 | tert-butyl 2-methylpropanoate group | benzhydryloxy group | —OH |
| 8 | tert-butyl 2-methylpropanoate group | 10,11-dihydro-5H-dibenzo[a,d]cyclohepten-5-yloxy group | —OH |
| 9 | tert-butyl 2-methylpropanoate group | (naphthalen-1-ylmethoxy) group | —OH |
| 10 | tert-butyl 2-methylpropanoate group | (anthracen-9-ylmethoxy) group | —OH |
| 11 | tert-butyl 2-methylpropanoate group | (9H-xanthen-9-ylmethoxy) group | —OH |

TABLE 1-continued
| Example # | A | Q | G |
|---|---|---|---|
| 12 | 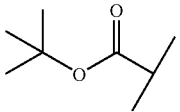 | 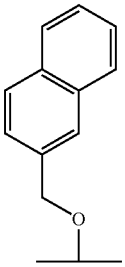 | 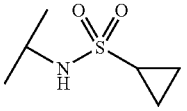 |
| 13 | 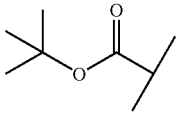 | 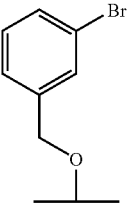 | 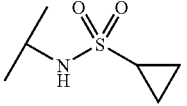 |
| 14 | 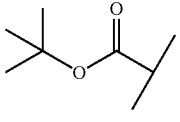 | 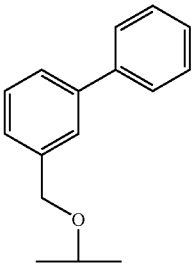 | 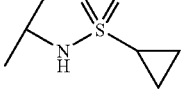 |
| 15 | 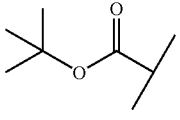 | 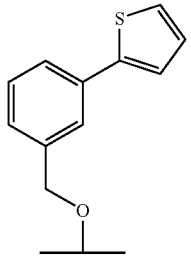 | 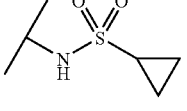 |
| 16 | 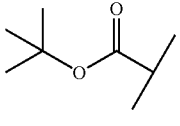 | 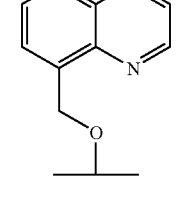 | 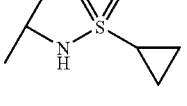 |
| 17 | 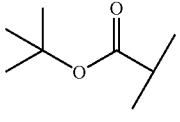 | 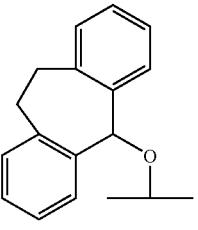 | 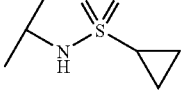 |

TABLE 1-continued
| Example # | A | Q | G |
|---|---|---|---|
| 18 | 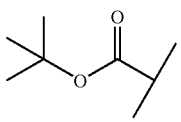 | 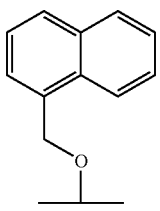 | 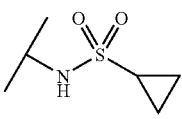 |
| 19 | 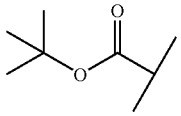 | 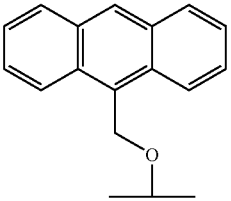 | 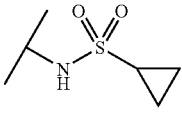 |
| 20 | 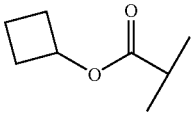 | 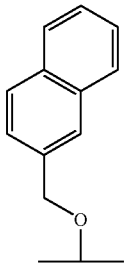 | 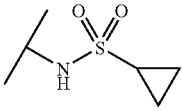 |
| 21 | 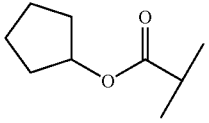 | 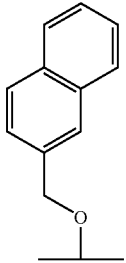 | 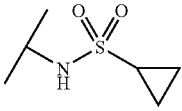 |
| 22 | 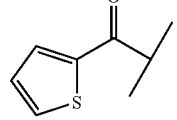 | 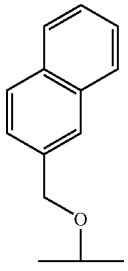 | 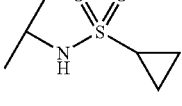 |
| 23 | 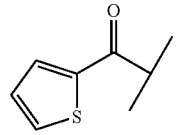 | 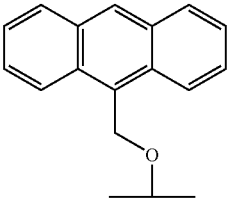 | 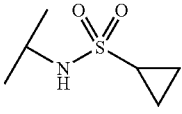 |

TABLE 1-continued
| Example # | A | Q | G |
|---|---|---|---|
| 24 | 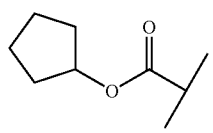 | 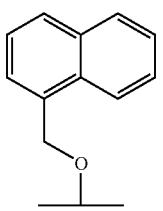 | 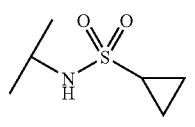 |
| 25 | 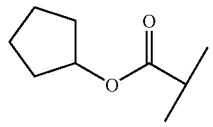 | 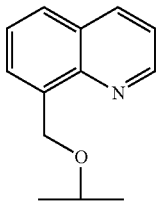 | 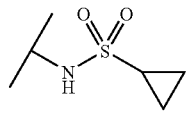 |
| 26 | 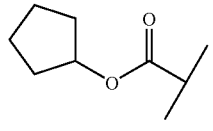 | 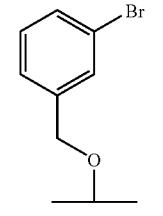 | 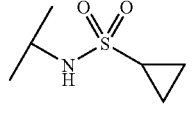 |
| 27 | 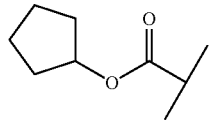 | 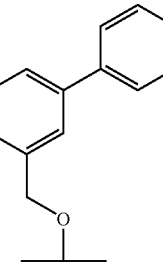 | 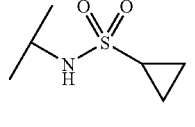 |
| 28 | 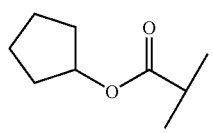 | 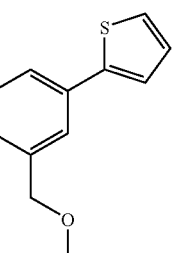 | 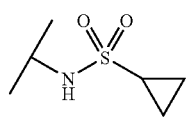 |
| 29 | 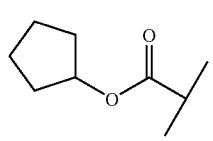 | 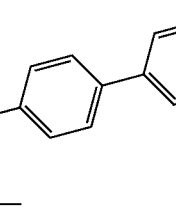 | 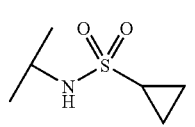 |

TABLE 1-continued
| Example # | A | Q | G |
|---|---|---|---|
| 30 | 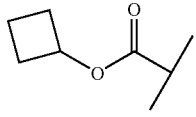 | 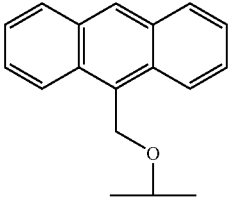 | 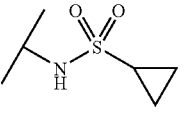 |
| 31 | 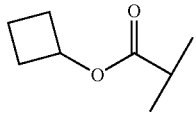 | 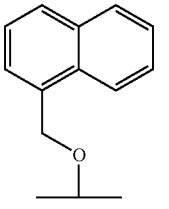 | 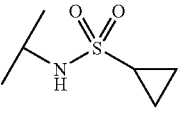 |
| 32 | 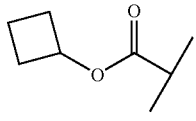 | 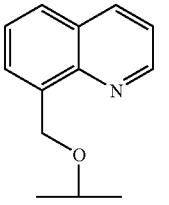 | 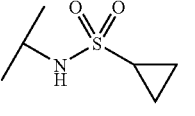 |
| 33 | 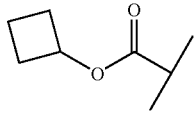 | 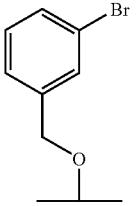 | 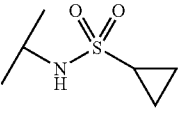 |
| 34 | 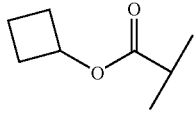 | 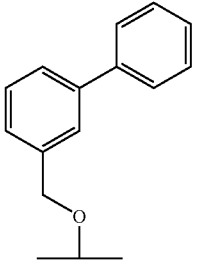 | 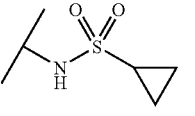 |
| 35 | 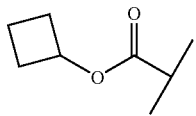 | 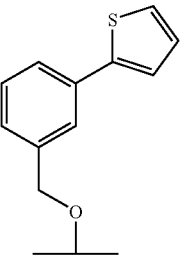 | 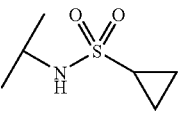 |

TABLE 1-continued
| Example # | A | Q | G |
|---|---|---|---|
| 36 | 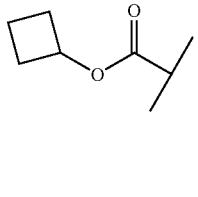 | 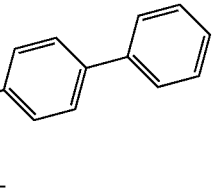 | 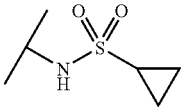 |
| 37 | 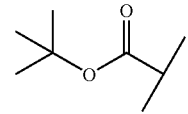 | 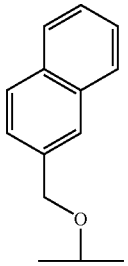 | 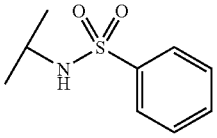 |
| 38 | 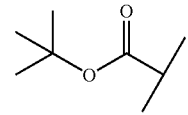 | 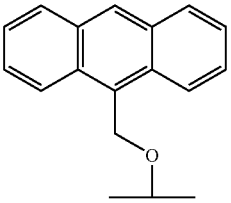 | 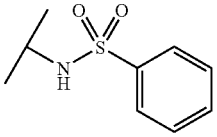 |
| 39 | 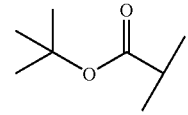 | 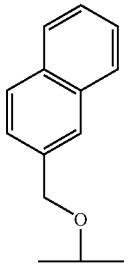 | 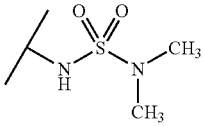 |
| 40 | 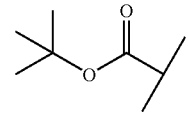 | 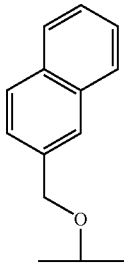 | 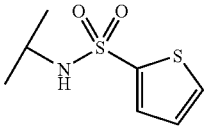 |

Representative compounds of the invention include, but are not limited to, the compounds 41-79 of the Formula XVI:
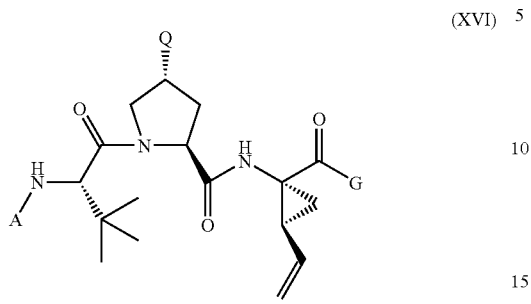
(XVI)
Wherein A, Q and G are delineated for each example in Table 2.
TABLE 2
| Example # | A | Q | G |
|---|---|---|---|
| 41 | | | —OH |
| 42 | | | |
| 43 | | | —OH |
| 44 | | | —OH |

TABLE 2-continued

| Example # | A | Q | G |
|---|---|---|---|
| 45 | tert-butyl isobutyrate ester | 3-bromobenzyl oxymethyl | —OH |
| 46 | tert-butyl isobutyrate ester | diphenylmethyl oxymethyl | —OH |
| 47 | tert-butyl isobutyrate ester | 10,11-dihydro-5H-dibenzo[a,d]cyclohepten-5-yl oxymethyl | —OH |
| 48 | tert-butyl isobutyrate ester | 1-naphthylmethyl oxymethyl | —OH |
| 49 | tert-butyl isobutyrate ester | 9-anthracenylmethyl oxymethyl | —OH |
| 50 | tert-butyl isobutyrate ester | 9H-xanthen-9-ylmethyl oxymethyl | —OH |
| 51 | tert-butyl isobutyrate ester | 2-phenylbenzyl oxymethyl | —OH |

TABLE 2-continued
| Example # | A | Q | G |
|---|---|---|---|
| 52 | 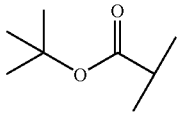 | 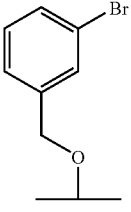 | 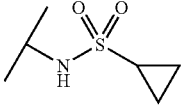 |
| 53 | 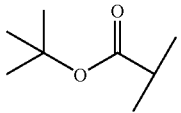 | 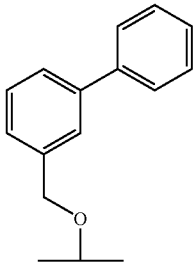 | 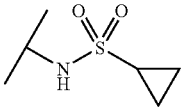 |
| 54 | 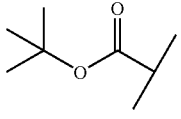 | 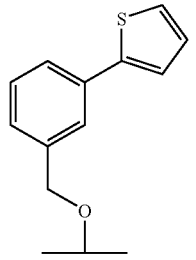 | 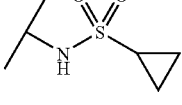 |
| 55 | 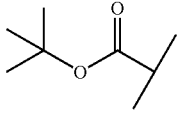 | 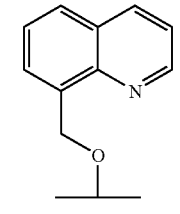 | 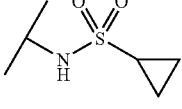 |
| 56 | 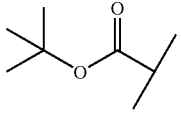 | 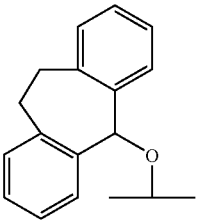 | 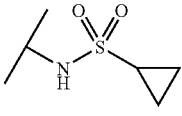 |
| 57 | 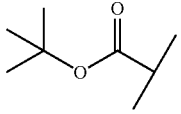 | 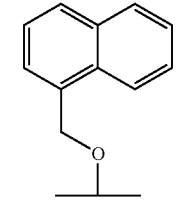 | 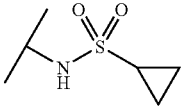 |

TABLE 2-continued
| Example # | A | Q | G |
|---|---|---|---|
| 58 | 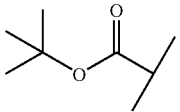 | 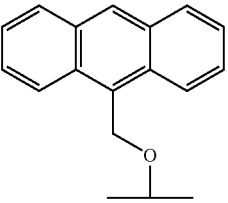 | 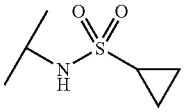 |
| 59 | 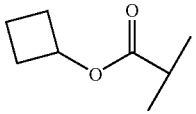 | 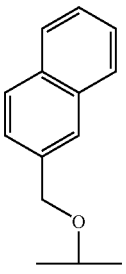 | 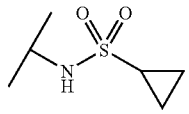 |
| 60 | 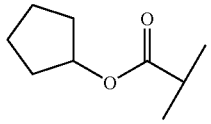 | 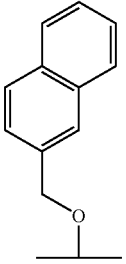 | 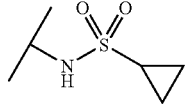 |
| 61 | 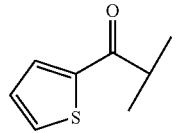 | 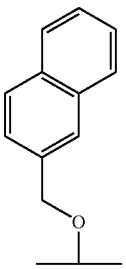 | 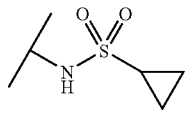 |
| 62 | 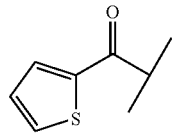 | 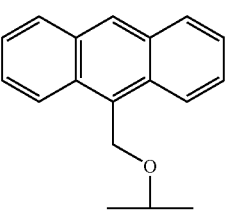 | 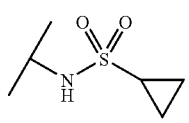 |
| 63 | 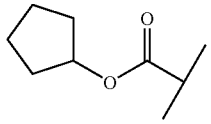 | 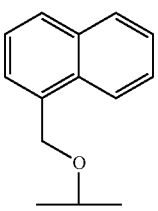 | 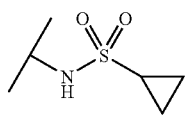 |

TABLE 2-continued
| Example # | A | Q | G |
|---|---|---|---|
| 64 | 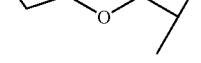 | 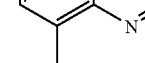 |  |
| 65 |  | 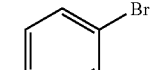 | 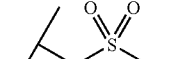 |
| 66 |  |  | 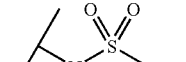 |
| 67 | 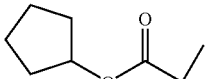 |  | 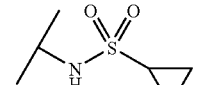 |
| 68 | 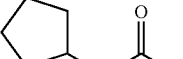 | 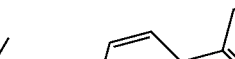 | 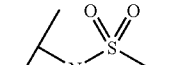 |
| 69 | 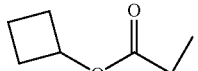 | 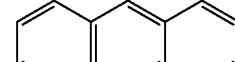 | 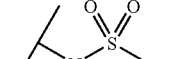 |

TABLE 2-continued
| Example # | A | Q | G |
|---|---|---|---|
| 70 | 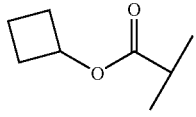 | 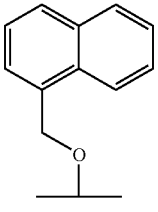 | 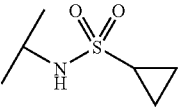 |
| 71 | 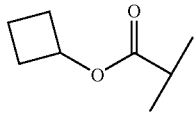 | 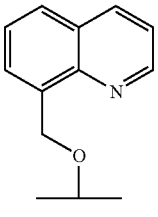 | 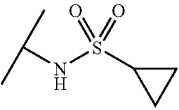 |
| 72 | 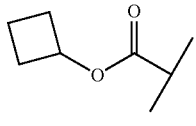 | 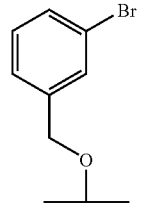 | 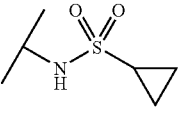 |
| 73 | 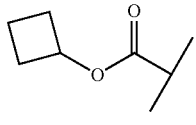 | 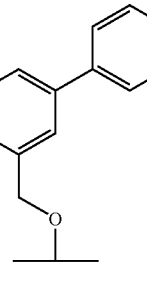 | 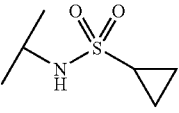 |
| 74 | 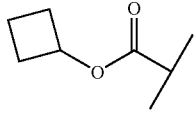 | 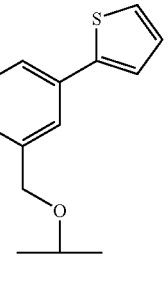 | 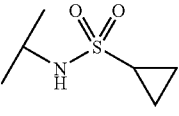 |
| 75 | 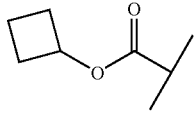 | 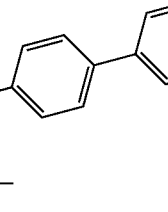 | 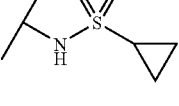 |

TABLE 2-continued

| Example # | A | Q | G |
|---|---|---|---|
| 76 | | | |
| 77 | | | |
| 78 | | | |
| 79 | | | |

The present invention also features pharmaceutical compositions comprising a compound of the present invention, or a pharmaceutically acceptable salt, ester or prodrug thereof.

According to an alternate embodiment, the pharmaceutical compositions of the present invention may further contain other anti-HCV agents. Examples of anti-HCV agents include, but are not limited to, interferon (e.g., alpha-interferon, beta-interferon, consensus interferon, pegylated interferon, or albumin or other conjugated interferon), ribavirin, and amantadine. For further details see S. Tan, A. Pause, Y. Shi, N. Sonenberg, Hepatitis C Therapeutics: Current Status and Emerging Strategies, *Nature Rev. Drug Discov.*, 1, 867-881 (2002); WO 00/59929 (2000); WO 99/07733 (1999); WO 00/09543 (2000); WO 99/50230 (1999); U.S. Pat. No. 5,861,297 (1999); and US2002/0037998 (2002) which are herein incorporated by reference in their entirety.

According to an additional embodiment, the pharmaceutical compositions of the present invention may further contain other HCV protease inhibitors.

According to yet another embodiment, the pharmaceutical compositions of the present invention may further comprise inhibitor(s) of other targets in the HCV life cycle, including, but not limited to, helicase, polymerase, metalloprotease, and internal ribosome entry site (IRES).

According to another embodiment, the pharmaceutical compositions of the present invention may further comprise another anti-viral, anti-bacterial, anti-fungal or anti-cancer agent, or an immune modulator, or another therapeutic agent.

According to still another embodiment, the present invention includes methods of treating hepatitis C infections in a subject in need of such treatment by administering to said subject an anti-HCV virally effective amount of a compound of the present invention or a pharmaceutically acceptable salt, ester, or prodrug thereof.

According to a further embodiment, the present invention includes methods of treating hepatitis C infections in a subject in need of such treatment by administering to said subject an anti-HCV virally effective amount or an inhibitory amount of a pharmaceutical composition of the present invention.

An additional embodiment of the present invention includes methods of treating biological samples by contacting the biological samples with the compounds of the present invention.

Yet a further aspect of the present invention is a process of making any of the compounds delineated herein employing any of the synthetic means delineated herein.

DEFINITIONS

Listed below are definitions of various terms used to describe this invention. These definitions apply to the terms as they are used throughout this specification and claims, unless otherwise limited in specific instances, either individually or as part of a larger group.

The terms "$C_1$-$C_6$ alkyl," or "$C_1$-$C_8$ alkyl," as used herein, refer to saturated, straight- or branched-chain hydrocarbon radicals containing between one and six, or one and eight carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl radicals include, but are not limited to, methyl, ethyl, propyl, isopropyl, n-butyl, tert-butyl, neopentyl, n-hexyl, heptyl, octyl radicals.

The terms "$C_2$-$C_6$ alkenyl," or "$C_2$-$C_8$ alkenyl," as used herein, denote a monovalent group derived from a hydrocarbon moiety containing from two to six, or two to eight carbon atoms having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl and the like.

The term "$C_2$-$C_6$ alkynyl," or "$C_2$-$C_8$ alkynyl," as used herein, denote a monovalent group derived from a hydrocarbon moiety containing from two to six, or two to eight carbon atoms having at least one carbon-carbon triple bond by the removal of a single hydrogen atom. Representative alkynyl groups include, but are not limited to, for example, ethynyl, 1-propynyl, 1-butynyl, heptynyl, octynyl and the like.

The term "$C_3$-$C_8$-cycloalkyl", or "$C_3$-$C_{12}$-cycloalkyl," as used herein, denotes a monovalent group derived from a monocyclic or polycyclic saturated carbocyclic ring compound by the removal of a single hydrogen atom, respectively. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo [2.2.1] heptyl, and bicyclo [2.2.2] octyl.

The term "$C_3$-$C_8$-cycloalkenyl", or "$C_3$-$C_{12}$-cycloalkenyl" as used herein, denote a monovalent group derived from a monocyclic or polycyclic carbocyclic ring compound having at least one carbon-carbon double bond by the removal of a single hydrogen atom. Examples of $C_3$-$C_8$-cycloalkenyl include, but not limited to, cyclopropenyl, cyclobutenyl, cyclopentenyl, cyclohexenyl, cycloheptenyl, cyclooctenyl, and the like; and examples of $C_3$-$C_{12}$-cycloalkenyl include, but not limited to, cyclopropenyl, cyclobutenyl, cyclopentenyl, cyclohexenyl, cycloheptenyl, cyclooctenyl, and the like.

The term "aryl," as used herein, refers to a mono- or bicyclic carbocyclic ring system having one or more aromatic rings including, but not limited to, phenyl, naphthyl, tetrahydronaphthyl, indanyl, idenyl and the like.

The term "arylalkyl," as used herein, refers to a $C_1$-$C_3$ alkyl or $C_1$-$C_6$ alkyl residue attached to an aryl ring. Examples include, but are not limited to, benzyl, phenethyl and the like.

The term "heteroaryl," as used herein, refers to a mono-, bi-, or tri-cyclic aromatic radical or ring having from five to ten ring atoms of which at least one ring atom is selected from S, O and N; wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroarylalkyl," as used herein, refers to a $C_1$-$C_3$ alkyl or $C_1$-$C_6$ alkyl residue attached to a heteroaryl ring. Examples include, but are not limited to, pyridinylmethyl, pyrimidinylethyl and the like.

The terms "heterocyclic" and "heterocycloalkyl," can be used interchangeably and referred to a non-aromatic 3-, 4-, 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "substituted" as used herein, refers to independent replacement of one, two, or three or more of the hydrogen atoms thereon with substituents including, but not limited to, —F, —Cl, —Br, —I, —OH, protected hydroxy, —NO$_2$, —CN, —NH$_2$, protected amino, —NH—$C_1$-$C_{12}$-alkyl, —NH—$C_2$-$C_{12}$-alkenyl, —NH—$C_2$-$C_{12}$-alkenyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkenyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkenyl, —C(O)—$C_3$-$C_{12}$-cycloalkyl, —C(O)-aryl, —C(O)-heteroaryl, —C(O)-heterocycloalkyl, —CONH$_2$, —CONH—$C_1$-$C_{12}$-alkyl, —CONH—$C_2$-$C_{12}$-alkenyl, —CONH—$C_2$-$C_{12}$-alkenyl, —CONH—$C_3$-$C_{12}$-cycloalkyl, —CONH-aryl, —CONH-heteroaryl, —CONH-heterocycloalkyl, —OCO$_2$—$C_1$-$C_{12}$-alkyl, —OCO$_2$—$C_2$-$C_{12}$-alkenyl, —OCO$_2$—$C_2$-$C_{12}$-alkenyl, —OCO$_2$—$C_3$-$C_{12}$-cycloalkyl, —OCO$_2$-aryl, —OCO$_2$-heteroaryl, —OCO$_2$-heterocycloalkyl, —OCONH$_2$, —OCONH—$C_1$-$C_{12}$-alkyl, —OCONH—$C_2$-$C_{12}$-alkenyl, —OCONH—$C_2$-$C_{12}$-alkenyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkenyl, —NHC(O)—$C_3$-$C_{12}$-cycloalkyl, —NHC(O)-aryl, —NHC(O)-heteroaryl, —NHC(O)-heterocycloalkyl, —NHCO$_2$—$C_1$-$C_{12}$-alkyl, —NHCO$_2$—$C_2$-$C_{12}$-alkenyl, —NHCO$_2$—$C_2$-$C_{12}$-alkenyl, —NHCO$_2$-$C_3$-$C_{12}$-cycloalkyl, —NHCO$_2$-aryl, —NHCO$_2$-heteroaryl, —NHCO$_2$-heterocycloalkyl, —NHC(O)NH$_2$, —NHC(O)NH—$C_1$-$C_{12}$-alkyl, —NHC(O)NH—$C_2$-$C_{12}$-alkenyl, —NHC(O)NH—$C_2$-$C_{12}$-alkenyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)NH$_2$, —NHC(S)NH-$C_1$-$C_{12}$-alkyl, —NHC(S)NH—$C_2$-$C_{12}$-alkenyl, —NHC(S)NH—$C_2$-$C_{12}$-alkenyl, —NHC(S)NH—$C_3$-$C_{12}$-cyloalkyl, —NHC(S)NH-aryl, —NHC(S)NH-heteroaryl, —NHC(S)NH-heterocycloalkyl, —NHC(NH)NH$_2$, —NHC(NH)NH—$C_1$-$C_{12}$-alkyl, —NHC(NH)NH—$C_2$-$C_{12}$-alkenyl, —NHC(NH)NH—$C_2$-$C_{12}$-alkenyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHCNH)—$C_1$-$C_{12}$-alkyl, —NHC(NH)—$C_2$-$C_{12}$-alkenyl, —NHC(NH)—$C_2$-$C_{12}$-alkenyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkenyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkenyl, —S(O)—$C_3$-$C_{12}$-cycloalkyl, —S(O)-aryl, —S(O)-heteroaryl, —S(O)-heterocycloalkyl, —$SO_2NH_2$, —$SO_2NH$—$C_1$-$C_{12}$-alkyl, —$SO_2NH$—$C_2$-$C_{12}$-alkenyl, —$SO_2NH$—$C_2$-$C_{12}$-alkenyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkenyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkenyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, and the like can be further substituted. In some cases, each substituent in a substituted moiety is additionally optionally substituted with one or more groups, each group being independently selected from —F, —Cl, —Br, —I, —OH, —$NO_2$, —CN, or —$NH_2$.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic," as used herein, denotes a monovalent group derived from a monocyclic or polycyclic saturated carbocyclic ring compound by the removal of a single hydrogen atom. Examples include, but not limited to, cyclopropyl, cyclobutyl, cyclopentyl, cyclohexyl, bicyclo [2.2.1] heptyl, and bicyclo [2.2.2] octyl. Such alicyclic groups may be further substituted.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycloalkylene, cycloalkenylene, cycloalkenylene, arylalkylene, hetoerarylalkylene and heterocycloalkylene groups are to be included in the above definitions, and are applicable to provide the formulas herein with proper valency.

The term "hydroxy activating group", as used herein, refers to a labile chemical moiety which is known in the art to activate a hydroxy group so that it will depart during synthetic procedures such as in a substitution or elimination reactions. Examples of hydroxy activating group include, but not limited to, mesylate, tosylate, triflate, p-nitrobenzoate, phosphonate and the like.

The term "activated hydroxy", as used herein, refers to a hydroxy group activated with a hydroxy activating group, as defined above, including mesylate, tosylate, triflate, p-nitrobenzoate, phosphonate groups, for example.

The term "protected hydroxy," as used herein, refers to a hydroxy group protected with a hydroxy protecting group, as defined above, including benzoyl, acetyl, trimethylsilyl, triethylsilyl, methoxymethyl groups.

The terms "halo" and "halogen," as used herein, refer to an atom selected from fluorine, chlorine, bromine and iodine.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

The term "hydroxy protecting group," as used herein, refers to a labile chemical moiety which is known in the art to protect a hydroxy group against undesired reactions during synthetic procedures. After said synthetic procedure(s) the hydroxy protecting group as described herein may be selectively removed. Hydroxy protecting groups as known in the are described generally in T. H. Greene and P. G., S. M. Wuts, *Protective Groups in Organic Synthesis,* 3rd edition, John Wiley & Sons, New York (1999). Examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilylethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxy protecting groups for the present invention are acetyl (Ac or —C(O)CH$_3$), benzoyl (Bz or —C(O)C$_6$H$_5$), and trimethylsilyl (TMS or —Si(CH$_3$)$_3$). Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound which is convertible in vivo by metabolic means (e.g. by hydrolysis) to afford any compound delineated by the formulae of the instant invention. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38 (1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, NY, 1986.

The terms "protogenic organic solvent," or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, NY, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Antiviral Activity

An inhibitory amount or dose of the compounds of the present invention may range from about 0.1 mg/kg to about 500 mg/kg, alternatively from about 1 to about 50 mg/kg. Inhibitory amounts or doses will also vary depending on route of administration, as well as the possibility of co-usage with other agents.

According to the methods of treatment of the present invention, viral infections are treated or prevented in a subject, such as a human or lower mammal, by administering to the subject an anti-hepatitis C virally effective amount or an inhibitory amount of a compound of the present invention, in such amounts and for such time as is necessary to achieve the desired result. An additional method of the present invention is the treatment of biological samples with an inhibitory amount of a compound of composition of the present invention in such amounts and for such time as is necessary to achieve the desired result.

The term "therapeutically effective amount" of a compound of the invention, as used herein, means a sufficient amount of the compound so as to decrease the viral load in a subject and/or decrease the subject's HCV symptoms. As is well understood in the medical arts a therapeutically effective amount of a compound of this invention will be at a reasonable benefit/risk ratio applicable to any medical treatment.

The term "anti-hepatitis C virally effective amount" of a compound of the invention, as used herein, mean a sufficient amount of the compound so as to decrease the viral load in a biological sample or in a subject. As well understood in the medical arts, an anti-hepatitis C virally effective amount of a compound of this invention will be at a reasonable benefit/risk ratio applicable to any medical treatment.

It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

The term "inhibitory amount" of a compound of the present invention means a sufficient amount to decrease the hepatitis C viral load in a biological sample or a subject. It is understood that when said inhibitory amount of a compound of the present invention is administered to a subject it will be at a reasonable benefit/risk ratio applicable to any medical treatment as determined by a physician. The term "biological sample(s)," as used herein, means a substance of biological origin intended for administration to a subject. Examples of biological samples include, but are not limited to, blood and components thereof such as plasma, platelets, subpopulations of blood cells and the like; organs such as kidney, liver, heart, lung, and the like; sperm and ova; bone marrow and components thereof, or stem cells. Thus, another embodiment of the present invention is a method of treating a biological sample by contacting said biological sample with an inhibitory amount of a compound or pharmaceutical composition of the present invention.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

An additional method of the present invention is the treatment of biological samples with an inhibitory amount of a compound of the present invention in such amounts and for such time as is necessary to inhibit viral replication and/or reduce viral load. The term "inhibitory amount" means a sufficient amount to inhibit viral replication and/or decrease the hepatitis C viral load in a biological sample. The term "biological sample(s)" as used herein means a substance of biological origin intended for administration to a subject. Examples of biological samples include, but are not limited to blood and components thereof such as plasma, platelets, subpopulations of blood cells and the like; organs such as kidney, liver, heart, lung, and the like; sperm and ova; bone marrow and components thereof, or stem cells. Thus another embodiment of the present invention is a method of treating a biological sample by contacting said biological sample with an inhibitory amount of a compound or pharmaceutical composition of the present invention.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:

ACN for acetonitrile;
Ac for acetyl;
Boc for tert-butoxycarbonyl;
Bz for benzoyl;
Bn for benzyl;
CDI for carbonyldiimidazole;
dba for dibenzylidene acetone;
CDI for 1,1'-carbonyldiimidizole;
DBU for 1,8-diazabicyclo[5.4.0]undec-7-ene;
DCM for dichloromethane;
DIAD for diisopropylazodicarboxylate;
DMAP for dimethylaminopyridine;
DMF for dimethyl formamide;
DMSO for dimethyl sulfoxide;
dppb for diphenylphosphino butane;
EtOAc for ethyl acetate;
HATU for 2-(7-Aza-1H-benzotriazole-1-yl)-1,1,3,3-tetramethyluronium hexafluorophosphate;
iPrOH for isopropanol;
NaHMDS for sodium bis(trimethylsilyl)amide;
NMO for N-methylmorpholine N-oxide;
MeOH for methanol;
Ph for phenyl;
POPd for dihydrogen dichlorobis(di-tert-butylphosphino)palladium(II);
TBAHS for tetrabutyl ammonium hydrogen sulfate;
TEA for triethylamine;
THF for tetrahydrofuran;
TPP for triphenylphosphine;
Tris for Tris(hydroxymethyl)aminomethane;
BME for 2-mercaptoethanol;
BOP for benzotriazol-1-yloxy-tris(dimethylamino)phosphonium hexafluorophosphate;
COD for cyclooctadiene;
DAST for diethylaminosulfur trifluoride;
DABCYL for 6-(N-4'-carboxy-4-(dimethylamino)azobenzene)-aminohexyl-1-O-(2-cyanoethyl)-(N,N-diisopropyl)-phosphoramidite;
DCM for dichloromethane;
DIAD for diisopropyl azodicarboxylate;
DIBAL-H for diisobutylaluminum hydride;
DIEA for diisopropyl ethylamine;
DMAP for N,N-dimethylaminopyridine;
DME for ethylene glycol dimethyl ether;
DMEM for Dulbecco's Modified Eagles Media;
EDANS for 5-(2-Amino-ethylamino)-naphthalene-1-sulfonic acid;
DMF for N,N-dimethyl formamide;
ESI for electrospray ionization;
Et DMSO for dimethylsulfoxide;
DUPHOS for

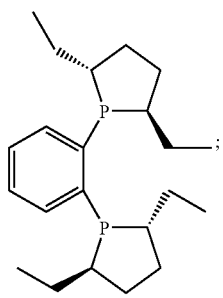

- EDANS for 5-(2-Amino-ethylamino)-naphthalene-1-sulfonic acid;
- EDCI or EDC for 1-(3-diethylaminopropyl)-3-ethylcarbodiimide hydrochloride;
- EtOAc for ethyl acetate;
- HATU for O (7-Azabenzotriazole-1-yl)-N,N,N',N'-tetramethyluronium hexafluorophosphate;
- Hoveyda's Cat. for Dichloro(o-isopropoxyphenylmethylene) (tricyclohexylphosphine)ruthenium(II);
- KHMDS is potassium bis(trimethylsilyl) amide;
- Ms for mesyl;
- NMM for N-4-methylmorpholine;
- PyBrOP for Bromo-tri-pyrrolidino-phosphonium hexafluorophosphate;
- Ph for phenyl;
- RCM for ring-closing metathesis;
- rt for room temperature;
- HATU for O-(7-Azabenzotriazole-1-yl)-N,N,N',N'-tetramethyluronium hexafluoro-phosphate;
- HPLC for high-performance liquid chromatography;
- Ph for phenyl;
- Me for methyl;
- RT for reverse transcription;
- RT-PCR for reverse transcription-polymerase chain reaction;
- TEA for triethyl amine;
- TFA for trifluoroacetic acid;
- MeOH for methanol;
- mg for milligram(s);
- min for minute(s);
- MS for mass spectrometry;
- NMR for nuclear magnetic resonance;
- rt for room temperature;
- THF for tetrahydrofuran;
- TLC for thin layer chromatography;
- TPP or PPh$_3$ for triphenylphosphine;
- tBOC or Boc for tert-butyloxy carbonyl; and
- Xantphos for 4,5-Bis-diphenylphosphanyl-9,9-dimethyl-9H-xanthene.

Synthetic Methods

The compounds and processes of the present invention will be better understood in connection with the following synthetic schemes that illustrate the methods by which the compounds of the invention may be prepared.

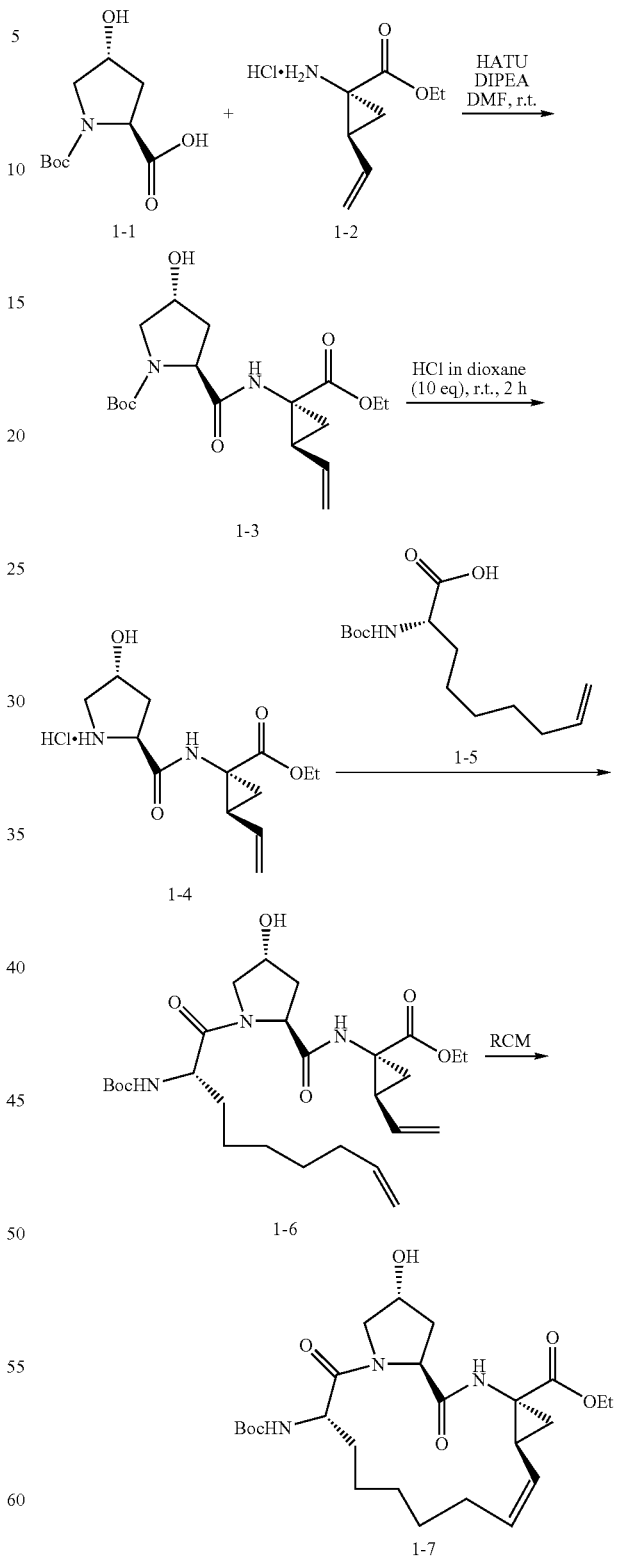

Scheme 1.

All of the 15-membered macrocyclic compounds of the present invention were prepared from the common intermediate 1-7. The synthesis of compound 1-7 is outlined in Scheme 1. Coupling of commercially available Trans-Boc-hydroxyproline 1-1 with cyclopropyl-containing amine 1-2 using HATU, afforded intermediate 1-3. Deprotection of 1-3 with HCl in dioxane followed by coupling with the acid 1-5 yielded tri-peptide 1-6. Other amino acid derivatives containing a terminal alkene may be used in place of 1-5 in order to generate varied macrocyclic structures (for further details see WO/0059929). Finally, ring-closing metathesis with a ruthenium-based catalyst gave the desired key intermediate 1-7 (for further details on ring closing metathesis see recent reviews: Grubbs et al., *Acc. Chem. Res.,* 1995, 28, 446; Shrock et al., *Tetrahedron* 1999, 55, 8141; Furstner, A. *Angew. Chem. Int. Ed.* 2000, 39, 3012; Trnka et al., *Acc. Chem. Res.* 2001, 34, 18; and Hoveyda et al., *Chem. Eur. J.* 2001, 7, 945).

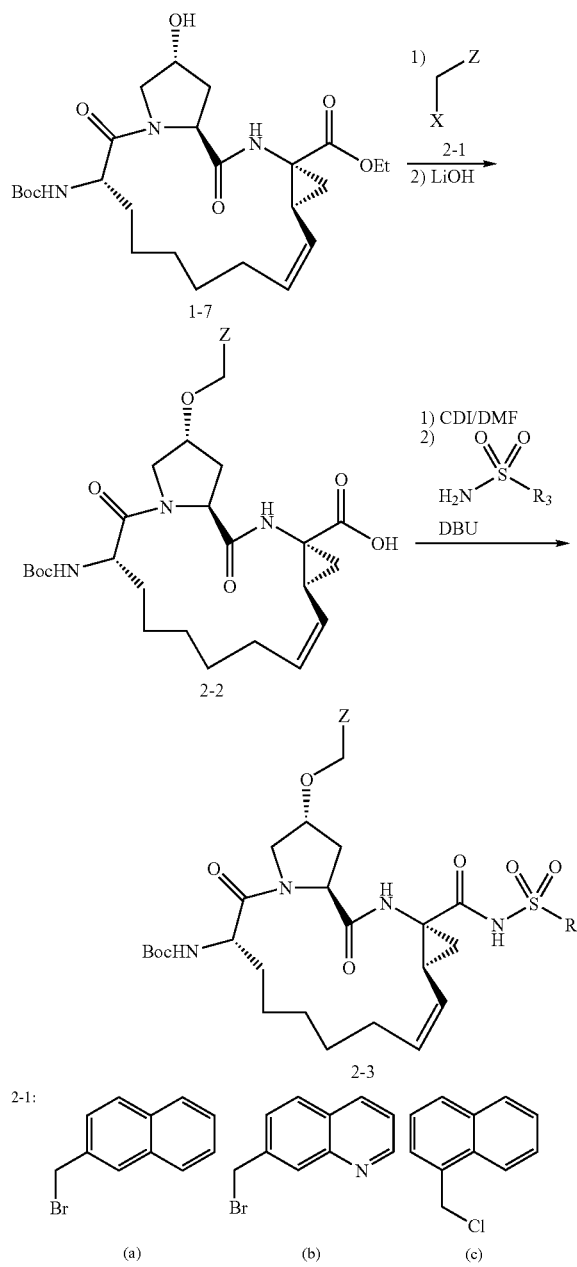

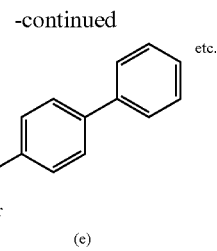

The arylalkyl substituted compounds 2-2 was prepared by an alkylation at the hydroxyl group on the proline. The typical conditions for the alkylation includes, but not limited to NaH/DMF, DBU/THF, KOH/DMF, NaOH aq. with phase transfer reagent, etc. The alkylating reagents include, but not limited to, compounds 2-1-a to 2-1-e as shown in Scheme 2. The alkylated intermediates were then hydrolyzed by LiOH in aq. methanol or THF to yield Compounds 2-2. The sulfonamides 2-3 were prepared from the corresponding acids 2-2 by subjecting the acid to a coupling reagent (i.e. CDI, HATU, DCC, EDC and the like) at RT or at elevated temperature, with the subsequent addition of the corresponding sulfonamide $R_3$—S$(O)_2$—$NH_2$ in the presence of base wherein $R_3$ and Z are as previously defined in Formula I.

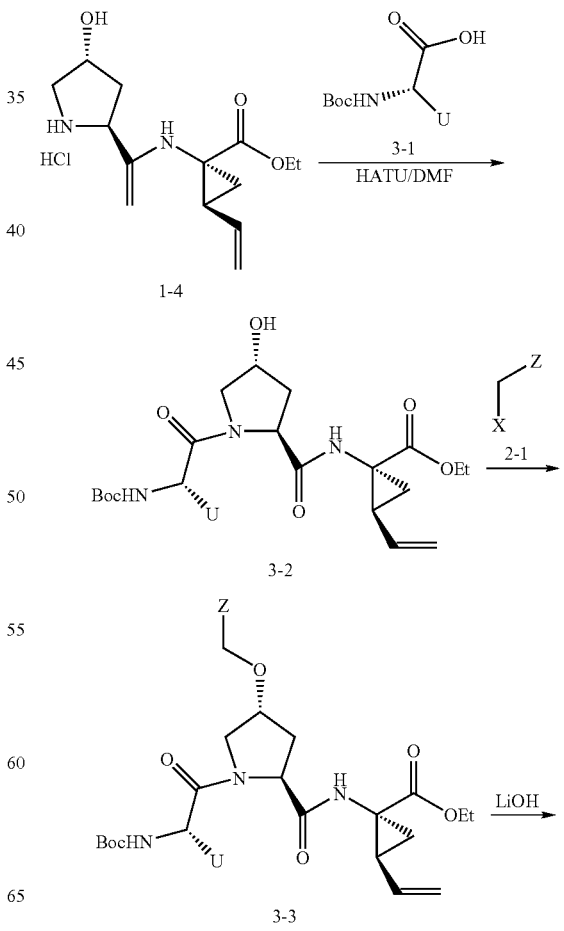

-continued

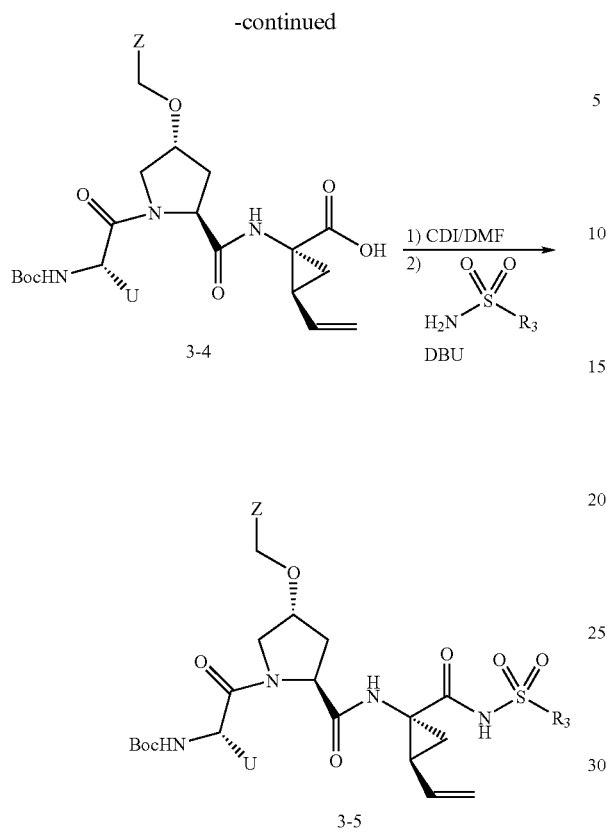

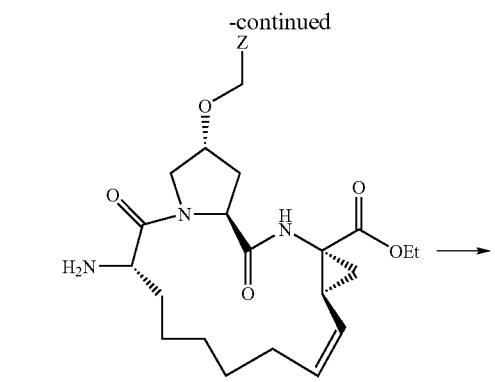

The tripeptide analogs 3-4 and 3-5 of the present invention were synthesized according Scheme 3. Similarly as described in Scheme 1, coupling of an amino acid 3-1 with the dipeptide 1-4 provided the tripeptide intermediate 3-2. The tripeptide intermediate 3-2 was then alkylated to form 3-3 followed by hydrolysis to afford the acids 3-4 as described in Scheme 2. The sulfonamides 3-5 were prepared from the corresponding acids 3-4 by subjecting the acid to a coupling reagent (i.e. CDI, HATU, DCC, EDC and the like) at RT or at elevated temperature, with the subsequent addition of the corresponding sulfonamide $R_3$—S(O)$_2$—NH$_2$ in the presence of base wherein $R_3$, U and Z are as previously defined in Formula I.

Scheme 4.

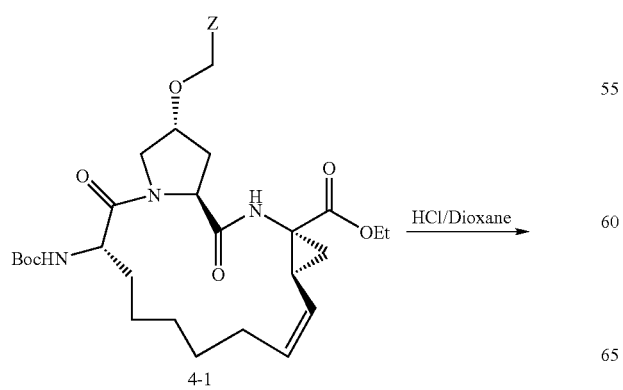

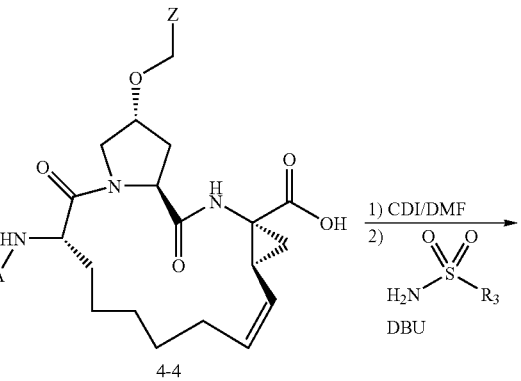

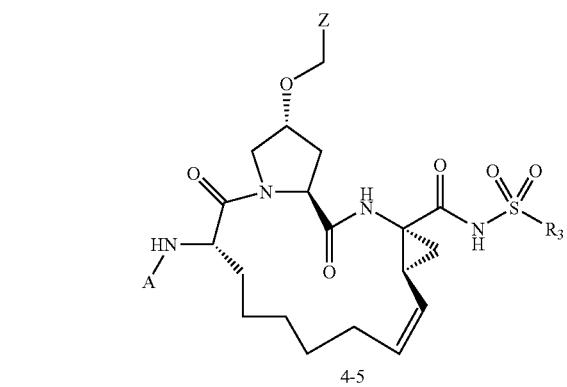

Scheme 4 illustrates the modification of the N-terminal of the macrocycle. Deprotection of the boc moiety with an acid, such as, but not limited to hydrochloric acid yields compounds of formula (4-2). The amino moiety of formula (4-2) can be alkylated or acylated with appropriate alkyl halide or acyl groups to give compounds of formula (4-3). Compounds of formula (4-3) can be hydrolyzed with base such as lithium hydroxide to free up the acid moiety of formula (4-4). Subsequent activation of the acid moiety (i.e. CDI, HATU, EDC and the like) followed by treatment with an sulfonamide including, but not limited to cyclopropylsulfonamide, phenyl sulfonamide, thienylsulfonamide, methyl sulfonamide etc. groups to provide compounds of formula (4-5), wherein A, Z and $R_3$ are as previously defined in Formula I.

Scheme 5.

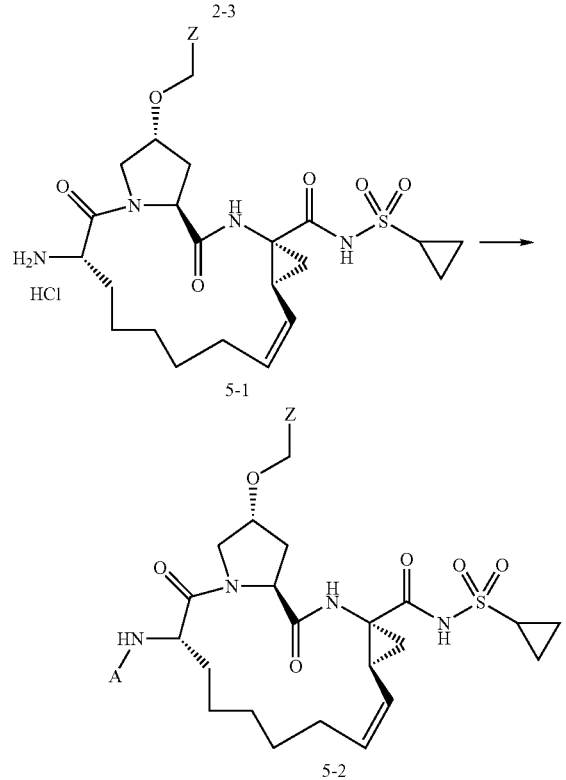

Scheme 5 illustrates an alternative method for the modification of the N-terminal of the macrocycle. Deprotection of the boc moiety of 2-3 with an acid, such as, but not limited to hydrochloric acid yields compounds of formula (5-1).) The amino moiety of formula (5-1) can be alkylated or acylated with appropriate alkyl halide or acyl groups to give compounds of formula (5-2). Wherein A and Z are as previously defined in Formula I.

The Modification of the N-terminal of the tripeptide compounds 3-4 and 3-5 are done by the same method outlined in Scheme 4 and 5.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples (example numbers correlate with numbers within table 1), which are intended as illustrations only and not to limit the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Synthesis of the Cyclic Peptide Precursor

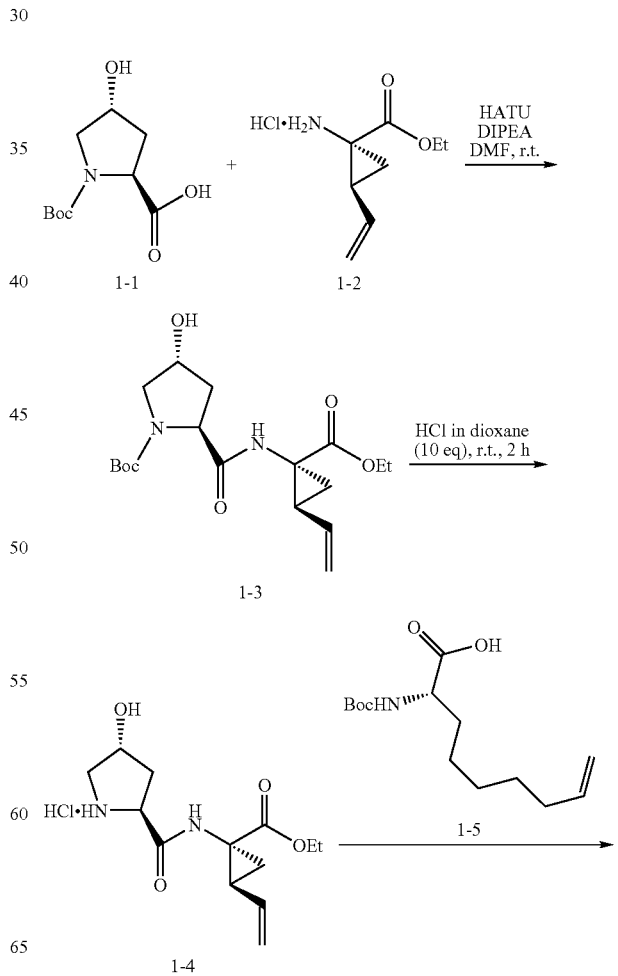

-continued

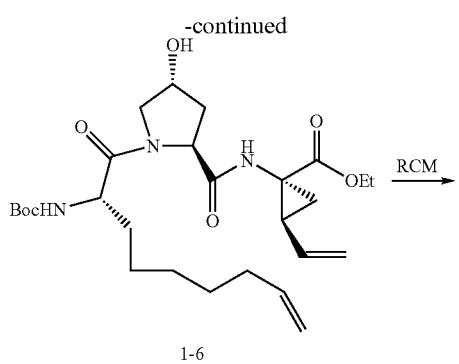

1-6

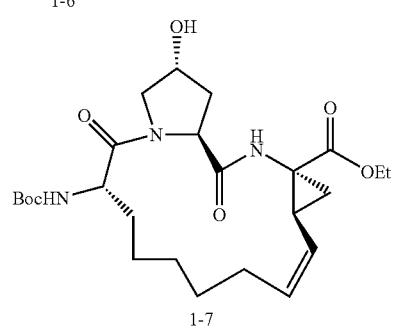

1-7

1A. To a solution of commercially available Trans-Boc-hydroxyproline 1-1 (12.72 g, 55 mol) and amino acid 1-2 (10.54 g, 55 mol) in 65 ml DMF was added HATU (20.9 g, 55 mmol) and DIEA (28.7 ml, 165 mmol). The coupling was carried out at 0° C. over a period of 1 hour. The reaction mixture was diluted with 500 mL EtOAc, and directly washed with 1M NaHCO$_3$ (4×100 ml) and brine (2×50 ml). The organic phase was dried over anhydrous Na$_2$SO$_4$, filtered, and then concentrated in vacuo, affording the dipeptide 1-3 that was identified by HPLC (Retention time=8.9 min, 30-70%, 90% B), and MS (found 369.18, M+H$^+$).

1B. Dipeptide 1-3 from step 1B was dissolved in 140 mL of 4N HCl in dioxane. The reaction mixture was stirred at room temperature for 2 h until LCMS showed the complete consumption of starting material. The solvent was removed in vacuo to afford the intermediate 1-4, MS (found 269.15, M+H$^+$).

1C. To a solution of Boc-L-2-amino-8-nonenoic acid 1-5 (14.9 g, 55 mol) and the compound from step 1B in 70 ml DMF was added HATU (20.9 g, 55 mmol) and DIEA (28.7 ml, 165 mmol). The coupling was carried out at 0° C. over a period of 1 hour. The reaction mixture was diluted with 500 mL EtOAc, and directly washed with 1M NaHCO$_3$ (4×100 ml) and brine (2×50 ml). The organic phase was dried over anhydrous Na$_2$SO$_4$, filtered, and then concentrated in vacuo, purified by flash column (Ethyl Acetate) to afford the tripeptide 1-6 (21.16 g, 74% 3 steps; MS: 522.29, M+H$^+$).

1D. Ring Closing Metathesis (RCM). A solution of the linear tripeptide 1-6 (10 g, 19.2 mmol) in 2.2 l anhydrous DCM was deoxygenated by N$_2$ bubbling. Hoveyda's 1$^{st}$ generation catalyst (8.5 mol % eq.) was then added as a solid. The reaction was refluxed under N$_2$ atmosphere for 12 hours. The solvent was evaporated and the residue was purified by silica gel flash chromatography using EtOAc. The cyclic peptide precursor 1-7 was isolated as a white powder (3.40, 36%, MS: 494.29 M+H).

Example 2

Compound of Formula XV, wherein

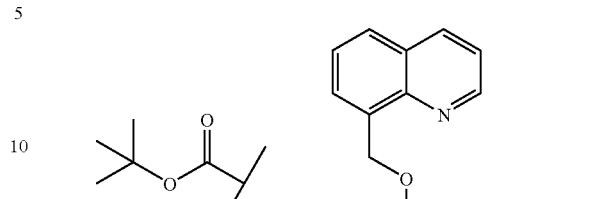

Step 2A.

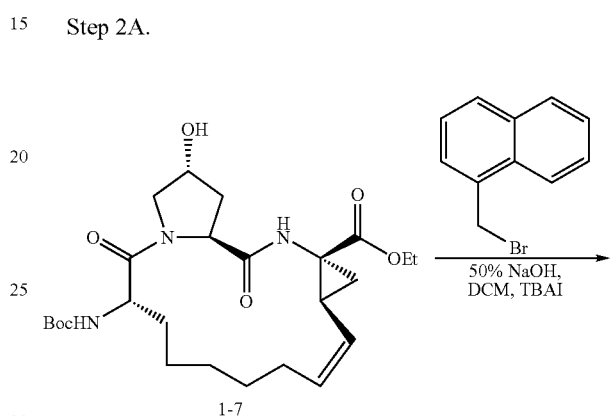

1-7

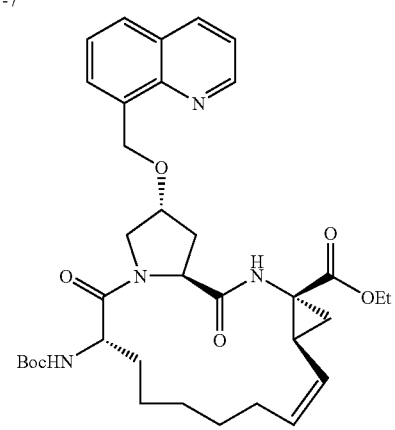

To a solution of macrocyclic precursor 1-7 (50 mg, 0.1 mmol) and 8-Bromomethyl-quinoline (28 mg, 0.12 mmol) in 3 ml methylene chloride was added 50% aq. NaOH (0.5 ml) and TBAI (tetrabutylammonium iodide, 5 mg, catalyst). The reaction mixture was stirred at RT for 1 hour. LC-MS showed the completion of the reaction. The aq. portion (at the bottom of container) was taken up and discarded. The organic layer was washed with saturated aqueous NaHCO3 solution, Water and brine consequently. The organic layer was dried over anhydrous sodium sulfate. The organic phase was then filtered, concentrated in vacuo to give a light yellow solid which was used directly in the next step.

MS (ESI) m/z 635.27 (M+H)$^+$.

Step 2B.

The compound of Step 2A and lithium hydroxide (10 equiv.) in THF/MeOH/H$_2$O (2:1:0.5) was stirred at room temperature for 10 hours. The excess solvents were evaporated in vacuo, and the resulting residue was diluted with water and acidified to pH ~5. The mixture was extracted with EtOAc (2×). The combined organic extracts were washed once with brine, dried (MgSO$_4$), filtered and concentrated in vacuo to give an oily residue, which was purified by column chromatography eluting with 2-10% methanol-chloroform to give the title compound (36.0 mg 60% for 2 steps).
MS (ESI) m/z 607.28 (M+H)$^+$.

Example 3

Compound of Formula XV, wherein

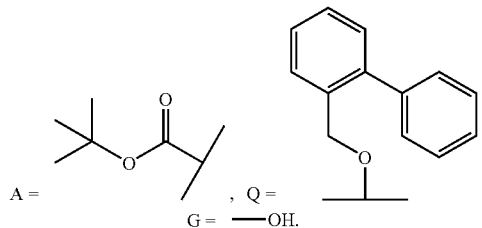

The title compound was prepared following the procedure described in Example 2 by starting with the corresponding halide.
MS (ESI) m/z 632.31 (M+H)$^+$.

Example 4

Compound of Formula XV, wherein

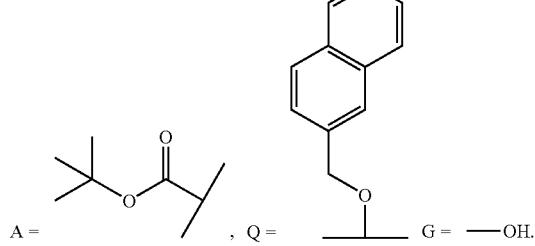

The title compound was prepared following the procedure described in Example 2 by starting with the corresponding halide.
MS (ESI) m/z 606.29 (M+H)$^+$.

Example 5

Compound of Formula XV, wherein

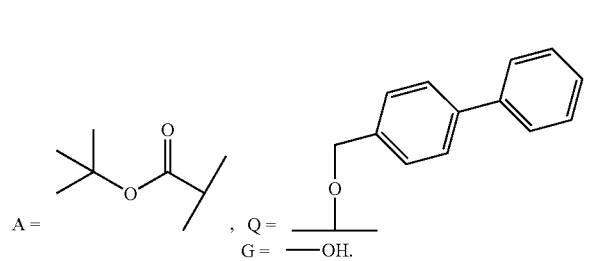

The title compound was prepared following the procedure described in Example 2 by starting with the corresponding halide.
MS (ESI) m/z 632.30 (M+H)$^+$.

Example 6

Compound of Formula XV, wherein

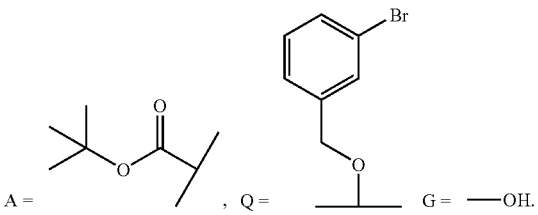

The title compound was prepared following the procedure described in Example 2 by starting with the corresponding halide.
MS (ESI) m/z 634.06, 636.06 (M+H)$^+$.

Example 7

Compound of Formula XV, wherein

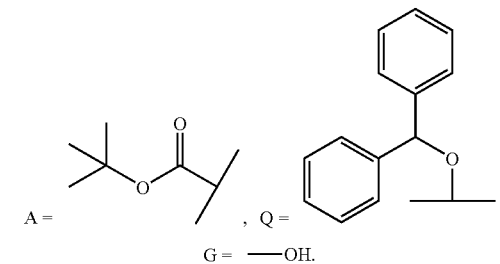

The title compound was prepared following the procedure described in Example 2 by starting with the corresponding halide.
MS (ESI) m/z 632.39 (M+H)$^+$.

Example 8

Compound of Formula XV, wherein

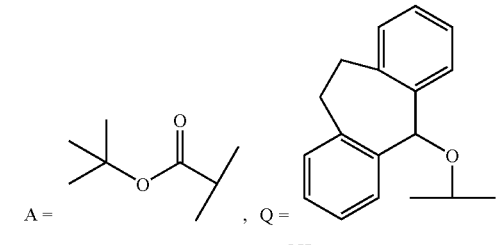

The title compound was prepared following the procedure described in Example 2 by starting with the corresponding halide.
MS (ESI) m/z 658.36 (M+H)$^+$.

Example 9

Compound of Formula XV, wherein

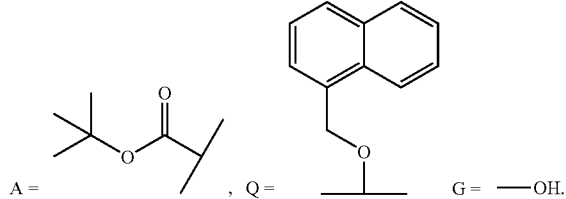

The title compound was prepared following the procedure described in Example 2 by starting with the corresponding halide.

MS (ESI) m/z 606.46 (M+H)$^+$.

Example 10

Compound of Formula XV, wherein

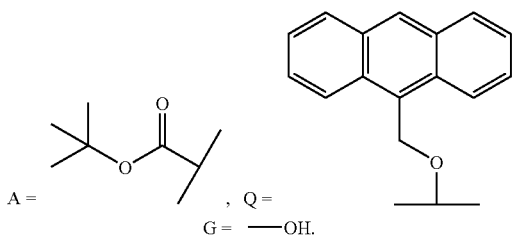

The title compound was prepared following the procedure described in Example 2 by starting with the corresponding halide.

MS (ESI) m/z 656.47 (M+H)$^+$.

Example 11

Compound of Formula XV, wherein

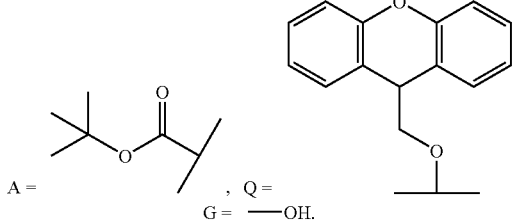

The title compound is prepared following the procedure described in Example 2 by starting with the corresponding halide.

Example 12

Compound of Formula XV, wherein

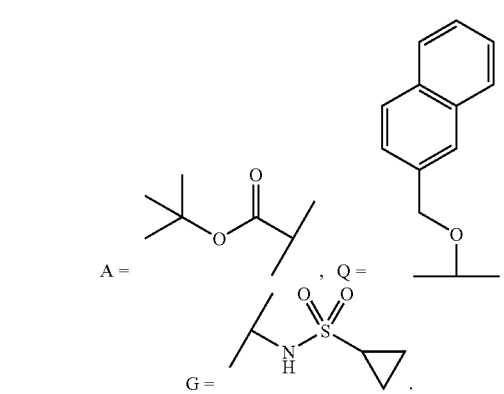

Step 12a: Cyclopropylsulfonyl chloride (1.4 g, 10 mmol) was dissolved in 0.5 M ammonia in dioxane (50 ml, 25 mmol) at RT. The reaction was kept at RT for 3 days. The large amount of precipitation was filtered and discarded. The clear filtrate was evaporated in vacuo and the white residue was dried on vacuum for 24 hours to give the cyclopropylsulfonamide (0.88 g, 74%). $^1$H-NMR (500 MHz, CD$_3$Cl): δ 4.62 (2H, s), 2.59 (1H, m), 1.20 (2H, m), 1.02 (2H, m).

Step 12b: The title compound from Example 4 (20.0 mg, 0.031 mmol) and carbonyldiimidazole (7.2 mg, 0.044 mmol) were dissolved in 1.0 ml anhydrous DMF and the resulting solution was heated to 40° C. for 1 hour. Cyclopropylsulfonamide (10.0 mg, 0.08 mmol) was added to the reaction followed by DBU (6.1 mg, 0.04 mmol). The reaction mixture was stirred at 40° C. for 10 hour. LCMS showed the formation of the desired product. The reaction was cooled down and 10 ml ethyl acetate was added to the solution. The mixture was washed with saturated aqueous NaHCO$_3$ solution, water and brine. The organic layer was dried over anhydrous sodium sulfate. The organic phase was then filtered, concentrated in vacuo and subsequently purified by flash chromatography (ethyl acetate/hexanes 1:1) to give 12.0 mg (52%) of the title compound.

MS (ESI) m/z 709.40 (M+H)$^+$.

Example 13

Compound of Formula XV, wherein

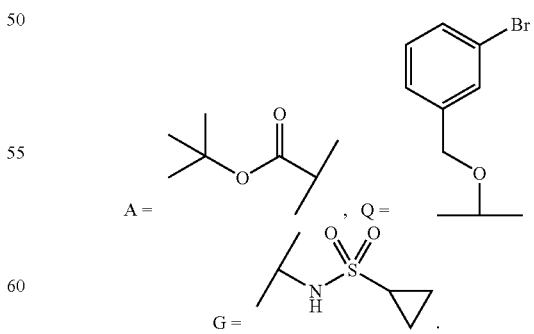

The title compound was prepared following the procedure described in Example 12 by starting with the title compound of Example 6.

MS (ESI) m/z 737.19/739.19 (M+H)$^+$.

Example 14

Compound of Formula XV, wherein

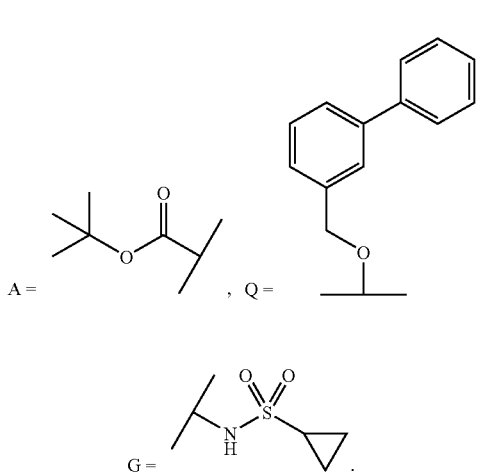

The title compound from Example 13 (20 mg, 0.027 mmol) and phenyltributyltin (13.0 mg, 0.035 mmol) were dissolved in 1.0 ml anhydrous toluene. The resulting solution was degassed and flushed with nitrogen. Tetrakis(triphenylphosphine)palladium (0) (4.0 mg, 0.003 mmol) was added to the reaction solution. The resulting mixture was heated to 100° C. for 2 hours. The solvent was then removed in vacuo and the residue was subsequently purified by flash chromatography (ethyl acetate/hexanes 1:1) to give 21.0 mg (100%) of the title compound.

MS (ESI) m/z 735.33 (M+H)$^+$.

Example 15

Compound of Formula XV, wherein

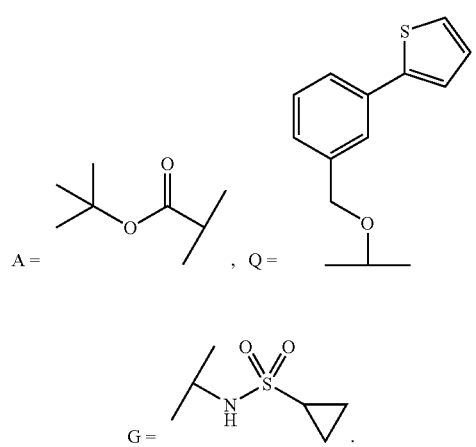

The title compound was prepared following the procedure described in Example 14 by using thienyltributyltin.

MS (ESI) m/z 741.37 (M+H)$^+$.

Example 16

Compound of Formula XV, wherein

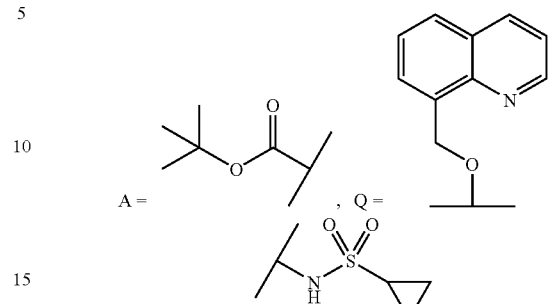

The title compound was prepared following the procedure described in Example 12 by starting with the title compound of Example 2.

MS (ESI) m/z 710.27 (M+H)$^+$.

Example 17

Compound of Formula XV, wherein

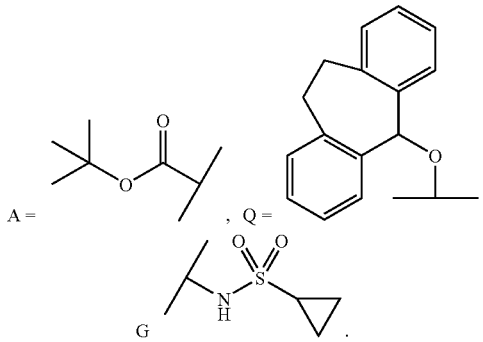

The title compound was prepared following the procedure described in Example 12 by starting with the title compound of Example 8.

MS (ESI) m/z 761.33 (M+H)$^+$.

Example 18

Compound of Formula XV, wherein

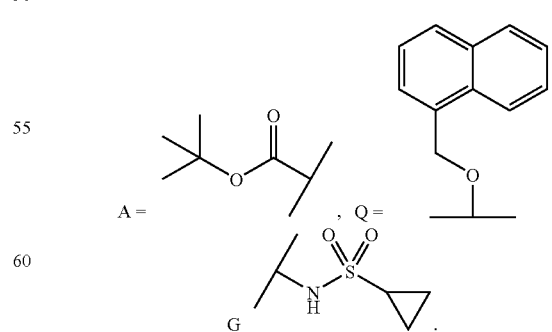

The title compound is prepared following the procedure described in Example 12 by starting with the title compound of Example 9.

Example 19

Compound of Formula XV, wherein

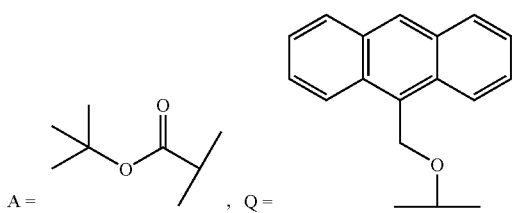

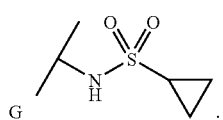

The title compound was prepared following the procedure described in Example 12 by starting with the title compound of Example 10.

MS (ESI) m/z 759.51 (M+H)$^+$.

Example 20

Compound of Formula XV, wherein

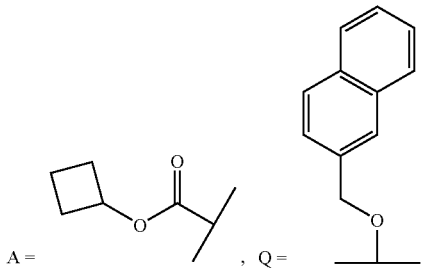

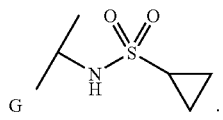

Step 20A. Amine Deprotection.

The title compound from Example 12 (177 mg, 0.25 mmol) was treated with HCl (4 M in dioxane, 5 mL, 20 mmol). The reaction mixture was stirred at room temperature for 1 h until LCMS showed the complete consumption of starting material. The solvent was removed in vacuo.

MS (ESI) m/z 609.42 (M+H)$^+$.

Step 20B. Chloroformate Reagent

The chloroformate reagent was prepared by dissolving 1.25 mmol of cyclobutanol in THF (5 ml) and adding 2.5 mmol of phosgene in toluene (20%). The resulting reaction mixture was stirred at room temperature for 2 hours and the solvent was removed in vacuo. To the residue was added DCM and subsequently concentrated to dryness twice in vacuo yielding chloroformate reagent.

Step 20C. Carbamate Formation

The resulting residue from step 20a (88.0 mg, 0.145 mmol) was dissolved in DCM (5.0 mL) then treated with cyclobutyl chloroformate prepared in step 20b (100 mg, 0.75 mmol) and iPr$_2$NEt (0.20 mL, excess). The reaction mixture was stirred for 10 h. Ethyl acetate (15 mL) was added to the solution. The mixture was washed with saturated aqueous NaHCO3 solution, Water and brine consequently. The organic layer was dried over anhydrous sodium sulfate. The organic phase was then filtered, concentrated in vacuo and subsequently purified by flash chromatography (Ethyl acetate/hexanes 1:1) to give 55.0 mg (55%) of the title compound.

MS (ESI) m/z 707.43 (M+H)$^+$.

Example 21

Compound of Formula XV, wherein

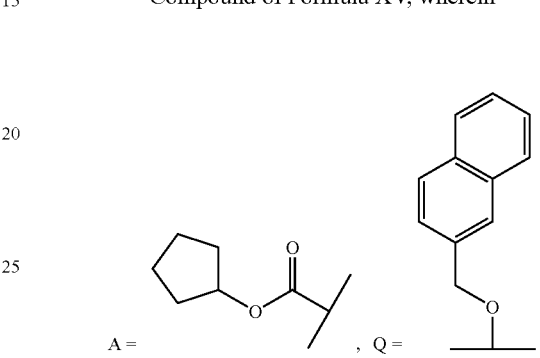

The title compound was prepared following the procedure described in Example 20 by using the cyclopentyl chloroformate.

MS (ESI) m/z 721.47 (M+H)$^+$.

Example 22

Compound of Formula XV, wherein

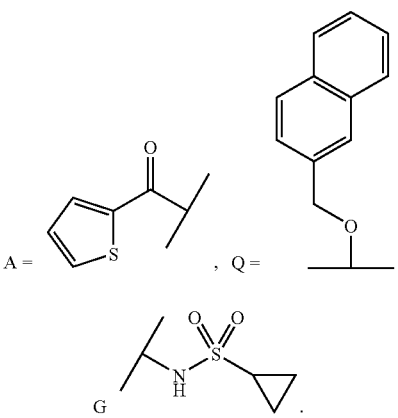

The title compound is prepared following the procedure described in Example 20 by using Thiophene-2-carboxylic acid and EDC in the place of the chloroformate.

Example 23

Compound of Formula XV, wherein

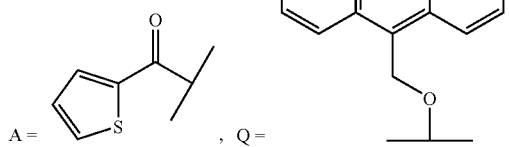

A = , Q =

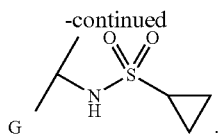

-continued

G

The title compound is prepared from the title compound of Example 19 following the procedure described in Example 20 by using Thiophene-2-carboxylic acid and EDC in the place of the chloroformate.

Additional compounds (Example 24-40) of the present invention that may be prepared via methods described in Examples 1-23 are shown in table 3 below:

TABLE 3

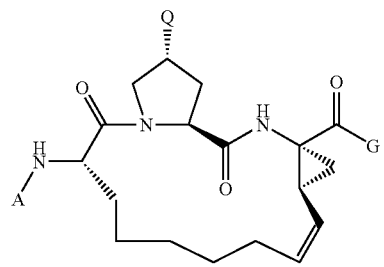

(XV)

| Example # | A | Q | G |
|---|---|---|---|
| 24 | 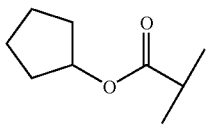 | 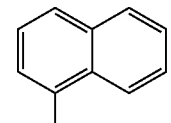 | 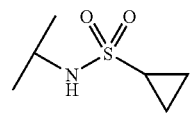 |
| 25 | 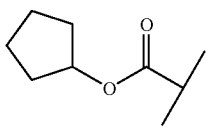 | 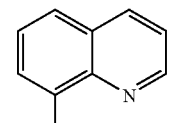 | 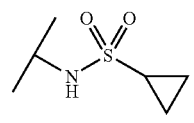 |
| 26 | 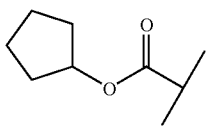 | 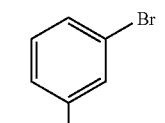 | 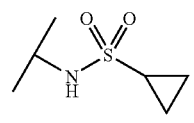 |
| 27 | 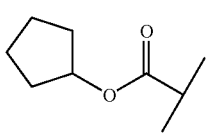 | 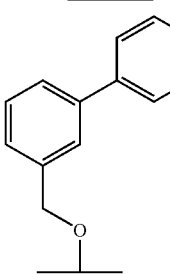 | 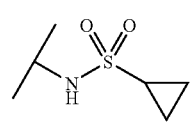 |

TABLE 3-continued (XV)

| Example # | A | Q | G |
|---|---|---|---|
| 28 | cyclopentyl ester isopropyl | 3-(thiophen-2-yl)benzyloxy | cyclopropylsulfonamide |
| 29 | cyclopentyl ester isopropyl | 4-phenylbenzyloxy | cyclopropylsulfonamide |
| 30 | cyclobutyl ester isopropyl | anthracen-9-ylmethoxy | cyclopropylsulfonamide |
| 31 | cyclobutyl ester isopropyl | naphthalen-1-ylmethoxy | cyclopropylsulfonamide |
| 32 | cyclobutyl ester isopropyl | quinolin-8-ylmethoxy | cyclopropylsulfonamide |
| 33 | cyclobutyl ester isopropyl | 3-bromobenzyloxy | cyclopropylsulfonamide |

TABLE 3-continued
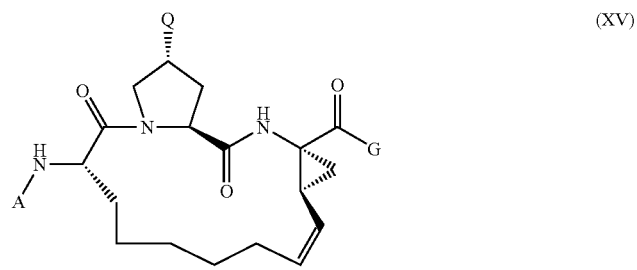
(XV)
| Example # | A | Q | G |
|---|---|---|---|
| 34 | 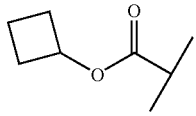 | 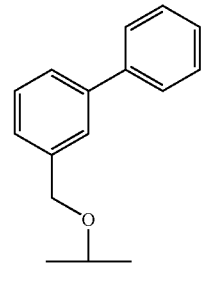 | 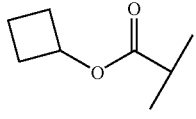 |
| 35 | 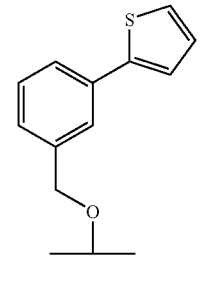 | 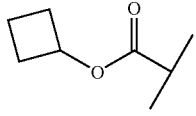 | 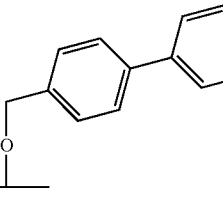 |
| 36 | 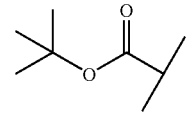 | 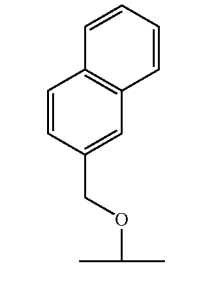 | |
| 37 | | | |

TABLE 3-continued
(XV)
| Example # | A | Q | G |
|---|---|---|---|
| 38 | *tert*-butyl isobutyrate group | anthracen-9-ylmethoxy group | N-phenylsulfonyl group |
| 39 | *tert*-butyl isobutyrate group | naphthalen-2-ylmethoxy group | N-(dimethylamino)sulfonyl group |
| 40 | *tert*-butyl isobutyrate group | naphthalen-2-ylmethoxy group | N-(thiophen-2-ylsulfonyl) group |
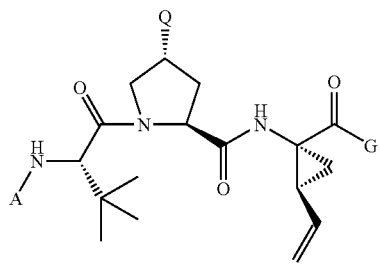
(XVI)

Example 41

Compound of Formula XVI, wherein

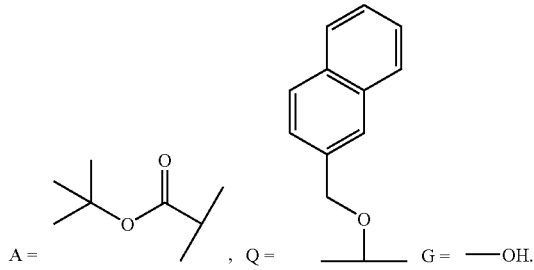

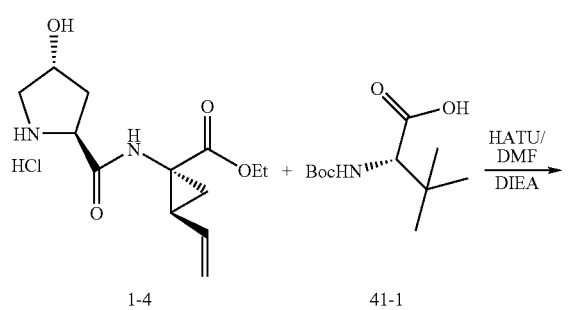

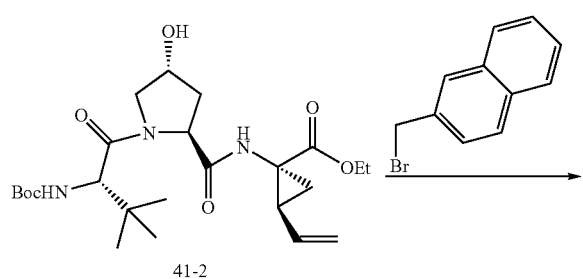

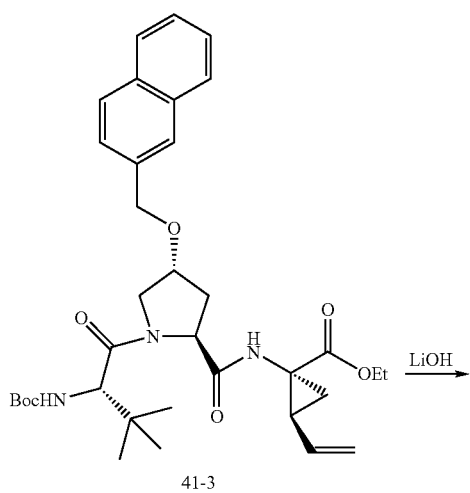

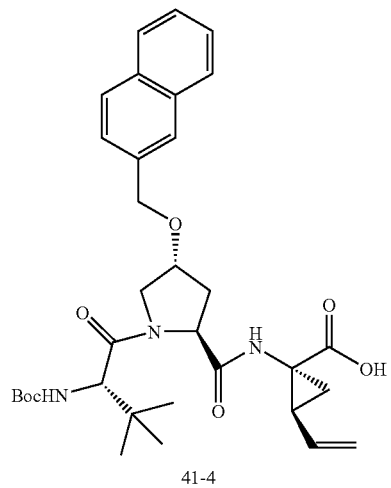

41-4

Step 41A. To a solution of Boc-L-tert-leucine 41-1 (0.37 g, 1.6 mmol), the compound from step 1B (1-4) (414 mg, 1.36 mmol), and DIEA (1.0 ml, 5.0 mmol) in DMF (3.0 ml) at 0° C. was added in HATU (0.6 g, 1.6 mmol). The mixture was stirred at rt for 10 h, diluted with EtOAc and washed with half-sat.-aq. NaCl four times. The organic phase was dried over anhydrous MgSO$_4$, filtered, and then concentrated in vacuo. The residue was purified by silica gel chromatography (Hexane/EtOAC=1:1 to 1:2) to afford the desired compound 41-2 (535 mg. 83%). MS (ESI): m/e 482.34 (M+H).

Step 41B. To a solution of the compound from step 41A (100 mg, 0.21 mmol) and 2-Bromomethyl-naphthalene (48 mg, 0.22 mmol) in 4 ml methylene chloride was added 50% aq. NaOH (0.2 ml) and TBAI (tetrabutylammonium iodide, 15 mg, catalyst). The reaction mixture was stirred at RT for 1 hour. LC-MS showed the completion of the reaction. The aq. portion (at the bottom of container) was taken up and discarded. The organic layer was washed with saturated aqueous NaHCO3 solution, Water and brine consequently. The organic layer was dried over anhydrous sodium sulfate. The organic phase was then filtered, concentrated in vacuo to give 41-3 as a light yellow solid which was used directly in the next step.

MS (ESI) m/z 622.39 (M+H)$^+$.

Step 41C. The compound of Step 41B and lithium hydroxide (10 equiv.) in THF/MeOH/H$_2$O (2:1:0.5) was stirred at room temperature for 10 hours. The excess solvents were evaporated in vacuo, and the resulting residue was diluted with water and acidified to pH ~5. The mixture was extracted with EtOAc (2×). The combined organic extracts were washed once with brine, dried (MgSO$_4$), filtered and concentrated in vacuo, and was purified by column chromatography eluting with 2-10% methanol-EtOAc to give the title compound 41-4 (120.0 mg 95% for 2 steps).

MS (ESI) m/z 594.37 (M+H)$^+$.

Example 42

Compound of Formula XVI, wherein

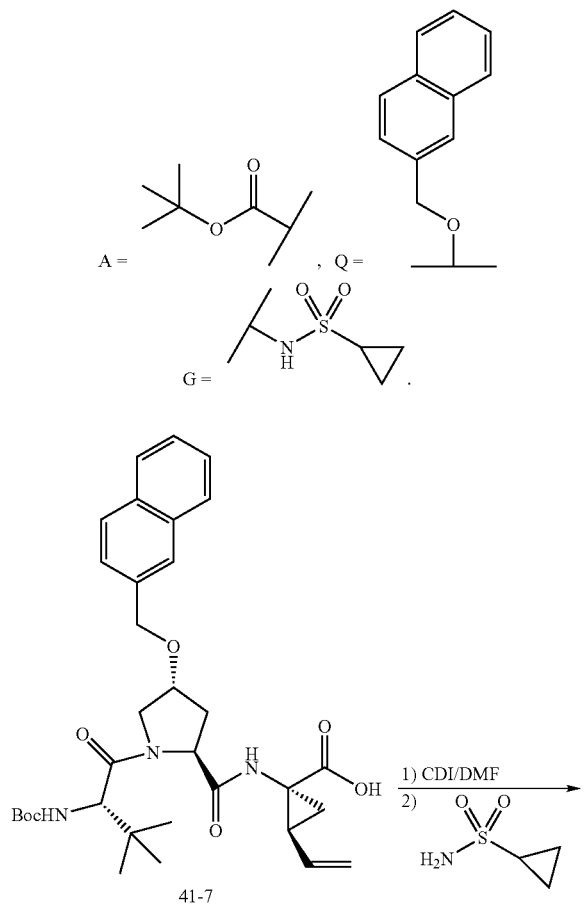

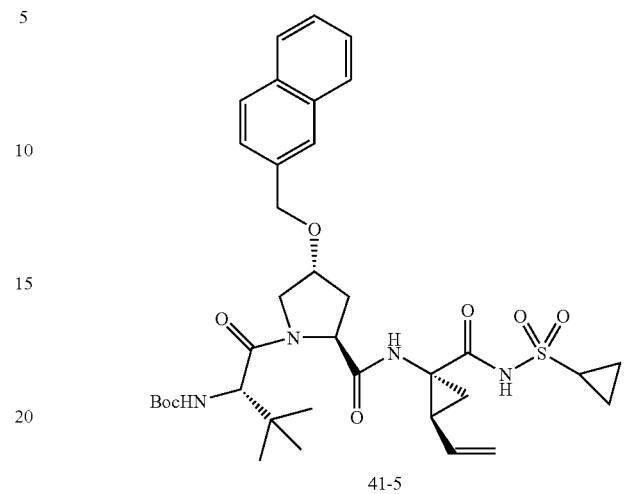

41-5

The title compound was prepared from the compound of Example 41 following the procedure described in Example 12.

MS (ESI) m/z 697.37 (M+H).

Additional compounds (Example 43-79) of the present invention that may be prepared via methods described in Example 41 are shown below in table 4. The general methods for such substitution on proline is either illustrated in Schemes 2 and 3, or in Examples 2-40 by substituting the macrocyclic core structures with the acyclic structure from Example 41.

TABLE 4

(XVI)

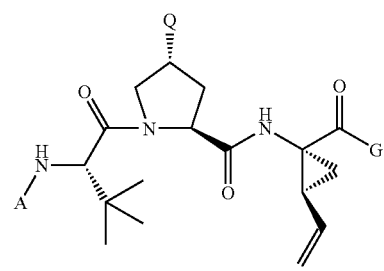

| Example # | A | Q | G |
|---|---|---|---|
| 43 | | | —OH |

TABLE 4-continued (XVI)

| Example # | A | Q | G |
|---|---|---|---|
| 44 | [tert-butyl ester-CH2-] | [4-biphenylmethoxy-] | —OH |
| 45 | [tert-butyl ester-CH2-] | [3-bromobenzyloxy-] | —OH |
| 46 | [tert-butyl ester-CH2-] | [diphenylmethoxy-] | —OH |
| 47 | [tert-butyl ester-CH2-] | [10,11-dihydro-5H-dibenzo[a,d]cycloheptenyloxy-] | —OH |
| 48 | [tert-butyl ester-CH2-] | [1-naphthylmethoxy-] | —OH |

TABLE 4-continued (XVI)

| Example # | A | Q | G |
|---|---|---|---|
| 49 | tert-butyl isobutyrate ester | 10-(isopropoxymethyl)anthracene | —OH |
| 50 | tert-butyl isobutyrate ester | 9-(isopropoxymethyl)-9H-xanthene | —OH |
| 51 | tert-butyl isobutyrate ester | 2-(isopropoxymethyl)biphenyl | —OH |
| 52 | tert-butyl isobutyrate ester | 3-bromo-(isopropoxymethyl)benzene | N-(cyclopropylsulfonyl)isopropylamine |
| 53 | tert-butyl isobutyrate ester | 3-(isopropoxymethyl)biphenyl | N-(cyclopropylsulfonyl)isopropylamine |

TABLE 4-continued (XVI)

| Example # | A | Q | G |
|---|---|---|---|
| 54 | tert-butyl ester of isobutyric acid | 3-(thiophen-2-yl)phenyl-CH₂-O- | cyclopropanesulfonamide |
| 55 | tert-butyl ester of isobutyric acid | quinolin-8-yl-CH₂-O- | cyclopropanesulfonamide |
| 56 | tert-butyl ester of isobutyric acid | 10,11-dihydro-5H-dibenzo[a,d]cyclohepten-5-yl-O- | cyclopropanesulfonamide |
| 57 | tert-butyl ester of isobutyric acid | naphthalen-1-yl-CH₂-O- | cyclopropanesulfonamide |
| 58 | tert-butyl ester of isobutyric acid | anthracen-9-yl-CH₂-O- | cyclopropanesulfonamide |

TABLE 4-continued
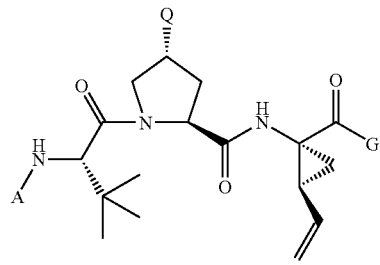
(XVI)
| Example # | A | Q | G |
|---|---|---|---|
| 59 | 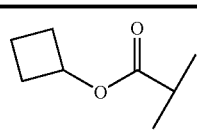 | 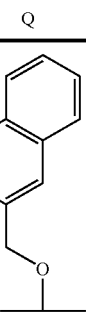 | 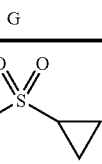 |
| 60 | 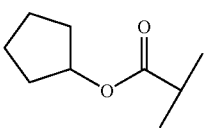 | 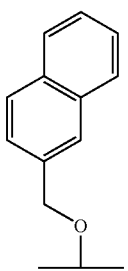 | 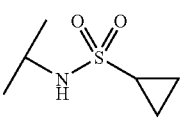 |
| 61 | 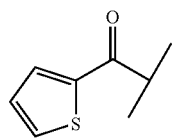 | 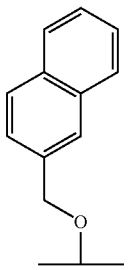 | 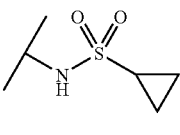 |
| 62 | 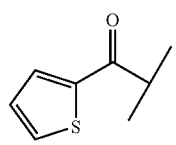 | 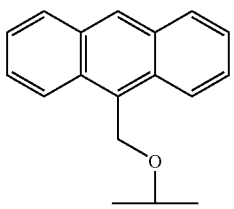 | 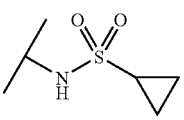 |
| 63 | 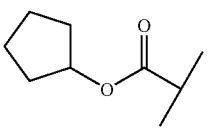 | 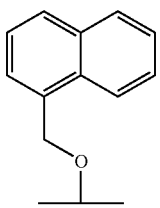 | 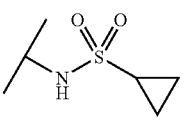 |

TABLE 4-continued

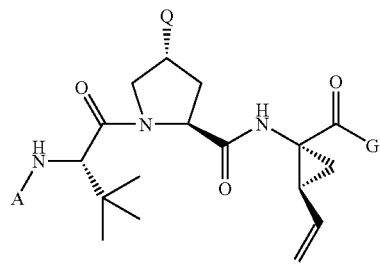

(XVI)

| Example # | A | Q | G |
|---|---|---|---|
| 64 | cyclopentyl ester isopropyl | quinolin-8-ylmethoxy | cyclopropanesulfonamide |
| 65 | cyclopentyl ester isopropyl | 3-bromobenzyloxy | cyclopropanesulfonamide |
| 66 | cyclopentyl ester isopropyl | biphenyl-3-ylmethoxy | cyclopropanesulfonamide |
| 67 | cyclopentyl ester isopropyl | 3-(thiophen-2-yl)benzyloxy | cyclopropanesulfonamide |
| 68 | cyclopentyl ester isopropyl | biphenyl-4-ylmethoxy | cyclopropanesulfonamide |

TABLE 4-continued
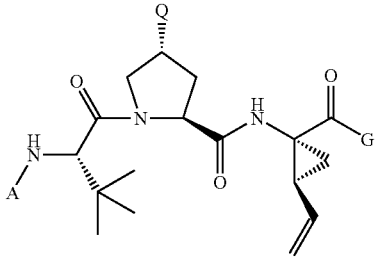

TABLE 4-continued
(XVI)
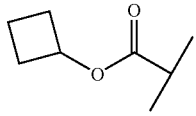
| Example # | A | Q | G |
|---|---|---|---|
| 74 | 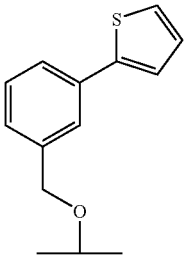 | 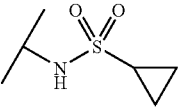 | 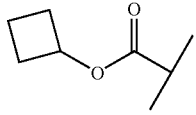 |
| 75 | 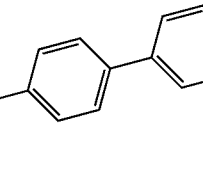 | 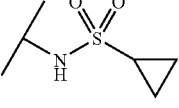 | 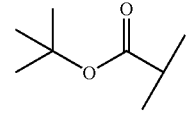 |
| 76 | 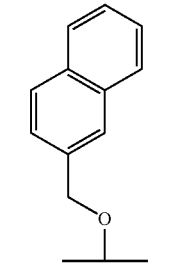 | 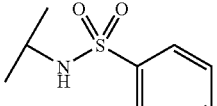 | 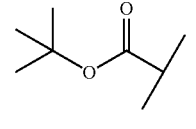 |
| 77 | 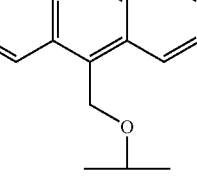 | 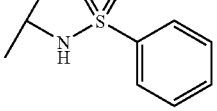 | 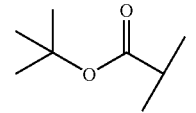 |
| 78 | 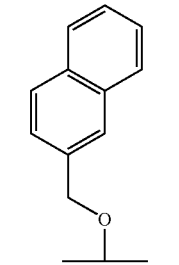 | 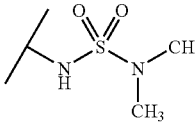 |  |

TABLE 4-continued

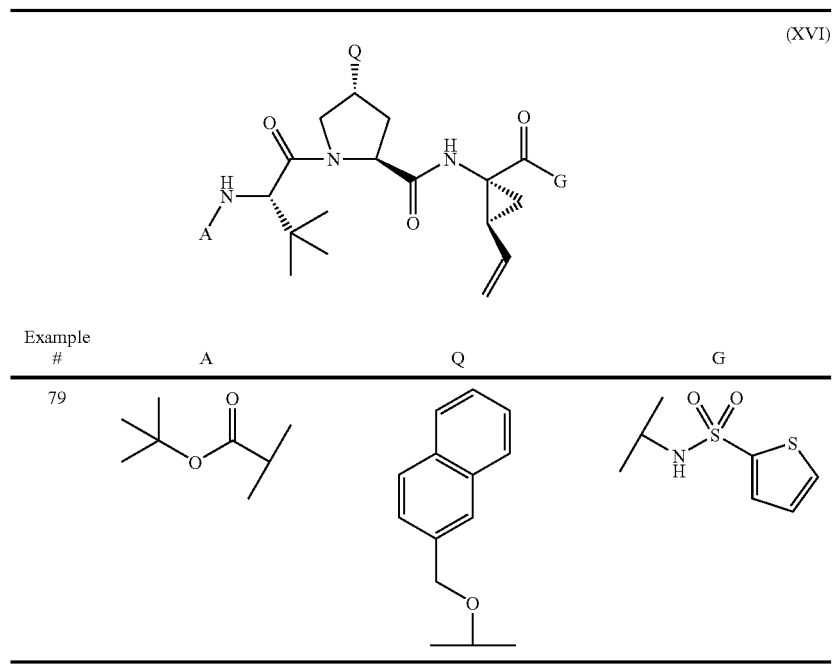

| Example # | A | Q | G |
|---|---|---|---|
| 79 | | | |

The compounds of the present invention exhibit potent inhibitory properties against the HCV NS3 protease. The following examples describe assays in which the compounds of the present invention can be tested for anti-HCV effects.

Example 80

NS3/NS4a Protease Enzyme Assay

HCV protease activity and inhibition is assayed using an internally quenched fluorogenic substrate. A DABCYL and an EDANS group are attached to opposite ends of a short peptide. Quenching of the EDANS fluorescence by the DABCYL group is relieved upon proteolytic cleavage. Fluorescence is measured with a Molecular Devices Fluoromax (or equivalent) using an excitation wavelength of 355 nm and an emission wavelength of 485 nm.

The assay is run in Corning white half-area 96-well plates (VWR 29444-312 [Corning 3693]) with full-length NS3 HCV protease 1b tethered with NS4A cofactor (final enzyme concentration 1 to 15 nM). The assay buffer is complemented with 10 μM NS4A cofactor Pep 4A (Anaspec 25336 or in-house, MW 1424.8). RET S1 (Ac-Asp-Glu-Asp(EDANS)-Glu-Glu-Abu-[COO]Ala-Ser-Lys-(DABCYL)-NH$_2$,- AnaSpec 22991, MW 1548.6) is used as the fluorogenic peptide substrate. The assay buffer contains 50 mM Hepes at pH 7.5, 30 mM NaCl and 10 mM BME. The enzyme reaction is followed over a 30 minutes time course at room temperature in the absence and presence of inhibitors.

The peptide inhibitors HCV Inh 1 (Anaspec 25345, MW 796.8) Ac-Asp-Glu-Met-Glu-Glu-Cys-OH, [−20° C.] and HCV Inh2 (Anaspec 25346, MW 913.1) Ac-Asp-Glu-Dif-Cha-Cys-OH, are used as reference compounds.

IC50 values are calculated using XLFit in ActivityBase (IDBS) using equation 205: $y=A+((B-A)/(1+((C/x)^D)))$ Example 81

Cell-Based Replicon Assay

Quantification of HCV replicon RNA (HCV Cell Based Assay) is accomplished using the Huh 11-7 cell line (Lohmann, et al Science 285:110-113, 1999). Cells are seeded at $4 \times 10^3$ cells/well in 96 well plates and fed media containing DMEM (high glucose), 10% fetal calf serum, penicillin-streptomycin and non-essential amino acids. Cells are incubated in a 7.5% $CO_2$ incubator at 37° C. At the end of the incubation period, total RNA is extracted and purified from cells using Ambion RNAqueous 96 Kit (Catalog No. AM 1812). To amplify the HCV RNA so that sufficient material can be detected by an HCV specific probe (below), primers specific for HCV (below) mediate both the reverse transcription of the HCV RNA and the amplification of the cDNA by polymerase chain reaction (PCR) using the TaqMan One-Step RT-PCR Master Mix Kit (Applied Biosystems catalog no. 4309169). The nucleotide sequences of the RT-PCR primers, which are located in the NS5B region of the HCV genome, are the following:

```
HCV Forward primer "RBNS5bfor"
5'GCTGCGGCCTGTCGAGCT:      (SEQ ID NO: 1)

HCV Reverse primer "RBNS5Brev"
5'CAAGGTCGTCTCCGCATAC.     (SEQ ID NO 2)
```

Detection of the RT-PCR product is accomplished using the Applied Biosystems (ABI) Prism 7500 Sequence Detection System (SDS) that detects the fluorescence that is emitted when the probe, which is labeled with a fluorescence reporter dye and a quencher dye, is degraded during the PCR reaction. The increase in the amount of fluorescence is measured during each cycle of PCR and reflects the increasing amount of RT-PCR product. Specifically, quantification is based on the threshold cycle, where the amplification plot crosses a defined fluorescence threshold. Comparison of the threshold cycles of the sample with a known standard provides a highly sensitive measure of relative template concentration in different samples (ABI User Bulletin #2 Dec. 11, 1997). The data is analyzed using the ABI SDS program version 1.7.

The relative template concentration can be converted to RNA copy numbers by employing a standard curve of HCV RNA standards with known copy number (ABI User Bulletin #2 Dec. 11, 1997).

The RT-PCR product was detected using the following labeled probe:

```
                                        (SEQ ID NO: 3)
   5' FAM-CGAAGCTCCAGGACTGCACGATGCT-TAMRA
```

FAM=Fluorescence reporter dye.

TAMRA:=Quencher dye.

The RT reaction is performed at 48° C. for 30 minutes followed by PCR. Thermal cycler parameters used for the PCR reaction on the ABI Prism 7500 Sequence Detection System are: one cycle at 95° C., 10 minutes followed by 40 cycles each of which include one incubation at 95° C. for 15 seconds and a second incubation for 60° C. for 1 minute.

To normalize the data to an internal control molecule within the cellular RNA, RT-PCR is performed on the cellular messenger RNA glyceraldehyde-3-phosphate dehydrogenase (GAPDH). The GAPDH copy number is very stable in the cell lines used. GAPDH RT-PCR is performed on the same RNA sample from which the HCV copy number is determined. The GAPDH primers and probesare contained in the ABI Pre-Developed TaqMan Assay Kit (catalog no. 4310884E). The ratio of HCV/GAPDH RNA is used to calculate the activity of compounds evaluated for inhibition of HCV RNA replication.

Activity of Compounds as Inhibitors of HCV Replication (Cell Based Assay) in replicon Containing Huh-7 Cell Lines.

The effect of a specific anti-viral compound on HCV replicon RNA levels in Huh-11-7cells is determined by comparing the amount of HCV RNA normalized to GAPDH (e.g. the ratio of HCV/GAPDH) in the cells exposed to compound versus cells exposed to the DMSO vehicle (negative control). Specifically, cells are seeded at $4 \times 10^3$ cells/well in a 96 well plate and are incubated either with: 1) media containing 1% DMSO (0% inhibition control), or 2) media/1% DMSO containing a fixed concentration of compound. 96 well plates as described above are then incubated at 37° C. for 4 days (EC50 determination). Percent inhibition is defined as:

% Inhibition=100−100*$S/C1$ where

S=the ratio of HCV RNA copy number/GAPDH RNA copy number in the sample;

C1=the ratio of HCV RNA copy number/GAPDH RNA copy number in the 0% inhibition control (media/1% DMSO).

The dose-response curve of the inhibitor is generated by adding compound in serial, three-fold dilutions over three logs to wells starting with the highest concentration of a specific compound at 1.5 uM and ending with the lowest concentration of 0.23 nM.

Further dilution series (500 nM to 0.08 nM for example) is performed if the EC50 value is not positioned well on the curve. EC50 is determined with the IDBS Activity Base program "XL Fit" using a 4-parameter, non-linear regression fit (model # 205 in version 4.2.1, build 16).

In the above assays, representative compounds are found to have activity.

Although the invention has been described with respect to various preferred embodiments, it is not intended to be limited thereto, but rather those skilled in the art will recognize that variations and modifications may be made therein which are within the spirit of the invention and the scope of the appended claims.

What is claimed is:

1. A compound represented by the formula (I) or (II):

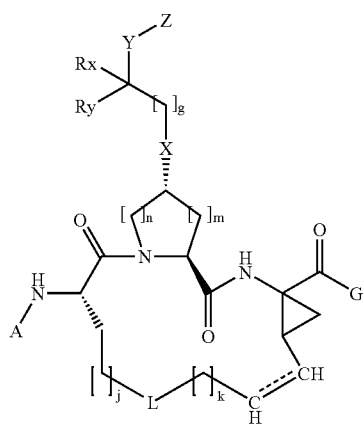

(I)

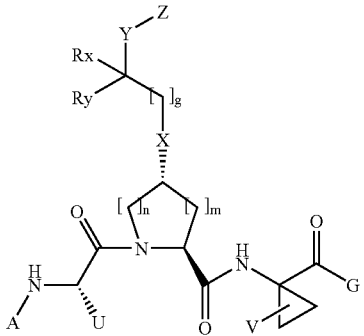

(II)

as well as the pharmaceutically acceptable salts and esters thereof, wherein:

A is selected from H, —(C═O)—O—$R_1$, —(C═O)$R_2$, —C(═O)—NH—$R_2$, —S(O)$_2$—$R_1$, and —S(O)$_2$NHR$_2$;

each $R_1$ is independently selected from the group consisting of:
(i) aryl;
(ii) substituted aryl;
(iii) heteroaryl;
(iv) substituted heteroaryl;
(v) Heterocycloalkyl;
(vi) substituted heterocycloalkyl;
(vii) —$C_1$-$C_8$ alkyl, —$C_2$-$C_8$ alkenyl, —$C_2$-$C_8$ alkynyl each containing 0, 1, 2, or 3 heteroatoms selected from O, S, or N;
(viii) substituted —$C_1$-$C_8$ alkyl, substituted —$C_2$-$C_8$ alkenyl, substituted $C_2$-$C_8$ alkynyl each containing 0, 1, 2, or 3 heteroatoms selected from O, S or N;
(ix) —$C_3$-$C_{12}$ cycloalkyl;
(x) substituted —$C_3$-$C_{12}$ cycloalkyl;
(xi) —$C_3$-$C_{12}$ cycloalkenyl; and
(xii) substituted —$C_3$-$C_{12}$ cycloalkenyl;

each $R_2$ is independently selected from the group consisting of:
(i) hydrogen;
(ii) aryl;
(iii) substituted aryl;
(iv) heteroaryl;
(v) substituted heteroaryl;
(vi) heterocycloalkyl;
(vii) substituted heterocycloalkyl;
(viii) —$C_1$-$C_8$ alkyl, —$C_2$-$C_8$ alkenyl, —$C_2$-$C_8$ alkynyl each containing 0, 1, 2, or 3 heteroatoms selected from 0, 5, or N;
(ix) substituted —$C_1$-$C_8$ alkyl, substituted —$C_2$-$C_8$ alkenyl, substituted —$C_2$-$C_8$ alkynyl each containing 0, 1, 2, or 3 heteroatoms selected from O, S or N;
(x) —$C_3$-$C_{12}$ cycloalkyl; or
(xi) substituted —$C_3$-$C_{12}$ cycloalkyl;
(xii) —$C_3$-$C_{12}$ cycloalkenyl; and
(xiii) substituted —$C_3$-$C_{12}$ cycloalkenyl;

G is selected from —OH, —NHS(O)$_2$—$R_3$, and —NH(SO$_2$)NR$_4$R$_5$;

each $R_3$ is independently selected from:
(i) aryl;
(ii) substituted aryl;
(iii) heteroaryl;
(iv) substituted heteroaryl;
(v) heterocycloalkyl;
(vi) substituted heterocycloalkyl;
(vii) —$C_1$-$C_8$ alkyl, —$C_2$-$C_8$ alkenyl, —$C_2$-$C_8$ alkynyl each containing 0, 1, 2, or 3 heteroatoms selected from O, S or N;
(viii) substituted —$C_1$-$C_8$ alkyl, substituted —$C_2$-$C_8$ alkenyl, substituted —$C_2$-$C_8$ alkynyl each containing 0, 1, 2, or 3 heteroatoms selected from O, S or N;
(ix) —$C_3$-$C_{12}$ cycloalkyl;
(x) substituted —$C_3$-$C_{12}$ cycloalkyl;
(xi) —$C_3$-$C_{12}$ cycloalkenyl; and
(xii) substituted —$C_3$-$C_{12}$ cycloalkenyl;

each $R_4$ and $R_5$ is independently selected from:

(i) hydrogen;
(ii) aryl;
(iii) substituted aryl;
(iv) heteroaryl;
(v) substituted heteroaryl;
(vi) heterocycloalkyl;
(vii) substituted heterocycloalkyl;
(viii) —$C_1$-$C_8$ alkyl, —$C_2$-$C_8$ alkenyl, —$C_2$-$C_8$ alkynyl each containing 0, 1, 2, or 3 heteroatoms selected from 0, 5, or N;
(ix) substituted —$C_1$-$C_8$ alkyl, substituted —$C_2$-$C_8$ alkenyl, substituted —$C_2$-$C_8$ alkynyl each containing 0, 1, 2, or 3 heteroatoms selected from O, S or N;
(x) —$C_3$-$C_{12}$ cycloalkyl;
(xi) substituted —$C_3$-$C_{12}$ cycloalkyl;
(xii) $C_3$-$C_{12}$ cycloalkenyl; and
(xiii) substituted $C_3$-$C_{12}$ cycloalkenyl;

L is selected from —$CH_2$—, —O—, S, $S(O)_2$, —CO—, —C(O)O—, —C(O)NH—, —CHF—, —$CF_2$—, aryl, substituted aryl, heteroaryl, and substituted heteroaryl;

U and V are independently selected from the group consisting of:
(i) hydrogen;
(ii) aryl; substituted aryl;
(iii) heteroaryl;
(iv) substituted heteroaryl;
(v) heterocyclic;
(vi) substituted heterocyclic;
(vii) —$C_1$-$C_8$ alkyl, —$C_2$-$C_8$ alkynyl, —$C_2$-$C_8$ alkynyl each containing 0, 1, 2, or 3 heteroatoms selected from O, S or N;
(viii) substituted —$C_1$-$C_8$ alkyl, substituted —$C_2$-$C_8$ alkenyl, substituted —$C_2$-$C_8$ alkynyl each containing 0, 1, 2, or 3 heteroatoms selected from O, S or N;
(ix) —$C_3$-$C_{12}$ cycloalkyl;
(x) substituted —$C_3$-$C_{12}$ cycloalkyl;
(xi) —$C_3$-$C_{12}$ cycloalkenyl; and
(xii) substituted —$C_3$-$C_{12}$ cycloalkenyl;

X is selected from the group consisting of:
(i) oxygen;
(ii) sulfur; and
(iii) $NR_4$; where $R_4$ is as previously defined above;

Y is absent or is selected from the group consisting of:
(i) —$C_1$-$C_6$ alkyl containing 0, 1, 2, or 3 heteroatoms selected from O, or N, optionally substituted with one or more substituents selected from halogen, aryl, substituted aryl, heteroaryl, and substituted heteroaryl;
(ii) —$C_2$-$C_6$ alkenyl containing 0, 1, 2, or 3 hetero atoms selected from O, or N, optionally substituted with one or more substituents selected from halogen, aryl, substituted aryl, heteroaryl, and substituted heteroaryl;
(iii) —$C_2$-$C_6$ alkynyl containing 0, 1, 2, or 3 heteroatoms selected from O, or N, optionally substituted with one or more substituents selected from halogen, aryl, substituted aryl, heteroaryl, and substituted heteroaryl;
(iv) —$C_3$-$C_{12}$ cycloalkyl;
(v) substituted —$C_3$-$C_{12}$ cycloalkyl;
(vi) heterocycloalkyl; and
(vii) substituted heterocycloalkyl;

Z is selected from aryl, substituted aryl, heteroaryl, and substituted heteroaryl;

Rx and Ry are each independently selected from a group consisting of:
(i) hydrogen;
(ii) aryl;
(iii) substituted aryl;
(iv) heteroaryl;
(v) substituted heteroaryl;
(vi) heterocycloalkyl;
(vii) substituted heterocycloalkyl;
(viii) —$C_1$-$C_8$ alkyl, —$C_2$-$C_8$ alkenyl, —$C_2$-$C_8$ alkynyl each containing 0, 1, 2, or 3 heteroatoms selected from O, S, or N;
(ix) substituted —$C_1$-$C_8$ alkyl, substituted —$C_2$-$C_8$ alkenyl, substituted —$C_2$-$C_8$ alkynyl each containing 0, 1, 2, or 3 heteroatoms selected from O, S or N;
(x) —$C_3$-$C_{12}$ cycloalkyl;
(xi) substituted —$C_3$-$C_{12}$ cycloalkyl
(xii) —$C_3$-$C_{12}$ cycloalkenyl; and
(xiii) substituted —$C_3$-$C_{12}$ cycloalkenyl;

or when Rx is not hydrogen and Y is not absent, Rx, taken together with W and Y form a ring structure shown in formula III or IV:

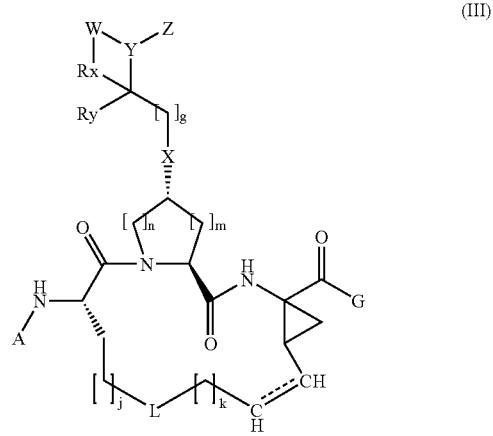

(III)

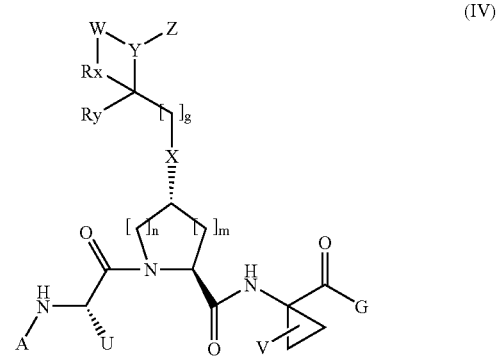

(IV)

wherein w is selected from $CH_2$, O, S, $NR_4R_5$, CO, $CH_2CH_2$, C(O)NH, $CH_2O$, $CH_2S$, and $CH_2NR_4$;

or when Rx is not hydrogen and Y is not absent, Rx, when taken together with W, Z, and Y form a ring structure as shown in formula V or VI:

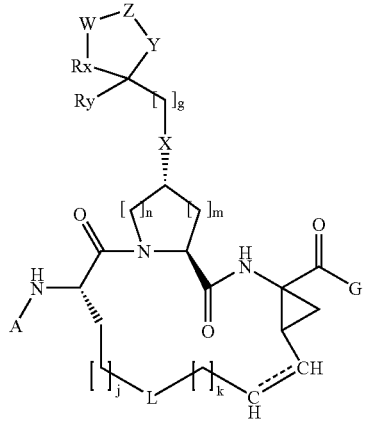

(V)

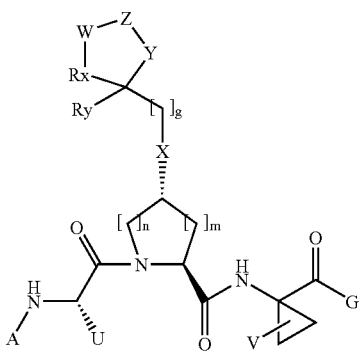

(VI)

g=0, 1, 2;
j=0, 1, 2, 3, or 4;
k=1, 2, or 3;
m=0, 1, or 2;
n=1, or 2; and
----- denotes a carbon-carbon single or double bond.

2. A compound according to claim 1 represented by formula VII or VIII:

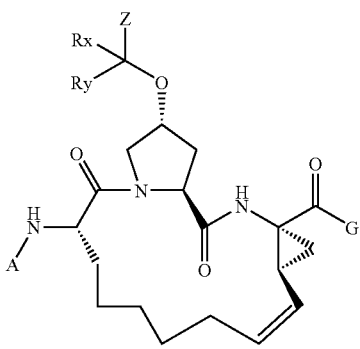

(VII)

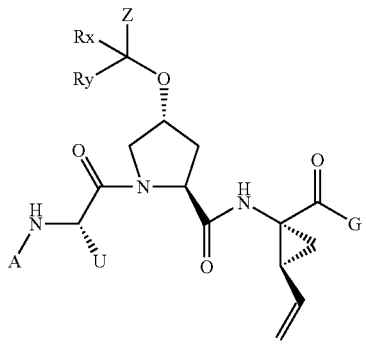

(VIII)

where A, G, Rx, Ry and Z are as defined in claim 1.

3. A compound according to claim 1 represented by formula IX or X:

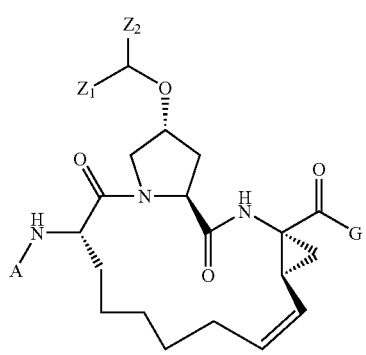

(IX)

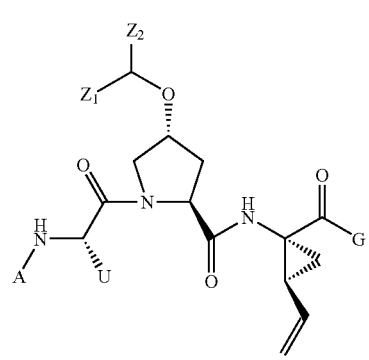

(X)

wherein each $Z_1$ and $Z_2$ is independently selected from aryl, substituted aryl, heteroaryl, and substituted heteroaryl; wherein A, G and U are as defined in claim 1.

4. A compound according to claim 1 represented by formula XI or XII:

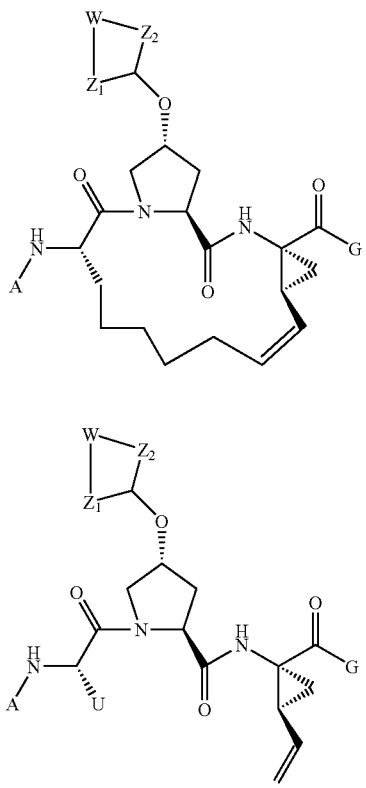

wherein each $Z_1$ and $Z_2$ is independently selected from aryl, substituted aryl, heteroaryl, and substituted heteroaryl; W is selected from $CH_2$, O, S, $NR_4R_5$, CO, $CH_2CH_2$, C(O)NH, $CH_2O$, $CH_2S$, $CH_2NR_4$; and wherein $R_4$, $R_5$, A, G and U are as defined in claim 1.

5. A compound according to claim 1 represented by formula XIII or XIV:

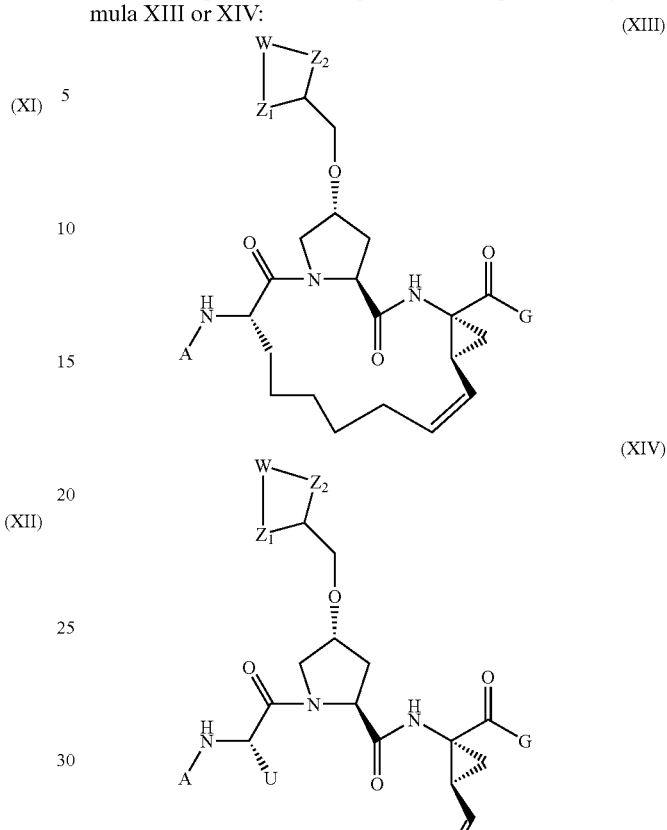

wherein each $Z_1$ and $Z_2$ is independently selected from aryl, substituted aryl, heteroaryl, and substituted heteroaryl; W is selected from $CH_2$, O, S, $NR_4R_5$, CO, $CH_2CH_2$, C(O)NH, $CH_2O$, $CH_2S$, and $CH_2NR_4R_5$; and wherein $R_4$, $R_5$, A, G and U are as defined in claim 1.

6. A compound of claim 1 having the Formula XV selected from compounds 2-40 of Table 1 wherein A, Q and G are defined in Table 1:

TABLE 1

(XV)

| Compound # | A | Q | G |
|---|---|---|---|
| 2 | *tert-butyl ester group* | *quinolin-8-ylmethoxy group* | —OH |

TABLE 1-continued
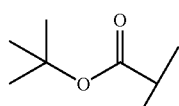
| Compound # | A | Q | G |
|---|---|---|---|
| 3 | 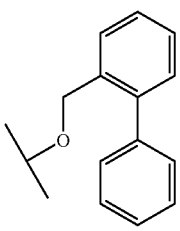 | 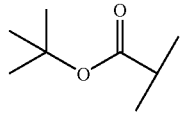 | —OH |
| 4 | 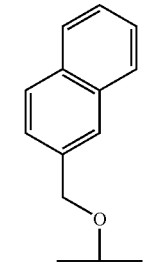 | 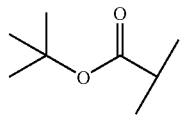 | —OH |
| 5 | 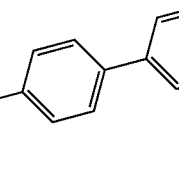 | 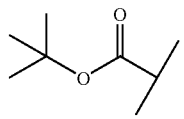 | —OH |
| 6 | 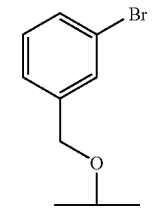 | 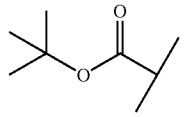 | —OH |
| 7 | 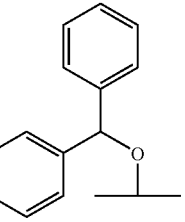 | | —OH |

TABLE 1-continued
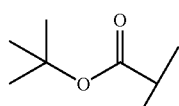
(XV)
| Compound # | A | Q | G |
|---|---|---|---|
| 8 | 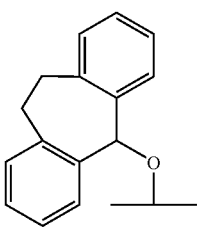 | 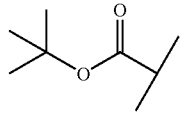 | —OH |
| 9 | 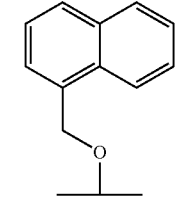 | 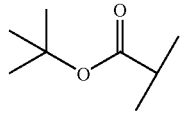 | —OH |
| 10 | 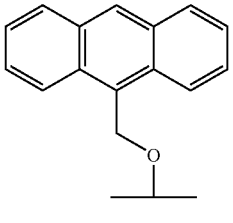 | 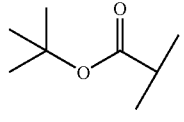 | —OH |
| 11 | 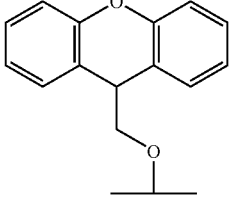 | 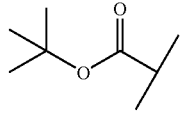 | —OH |
| 12 | 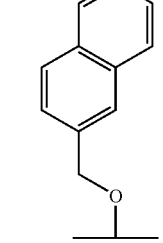 | 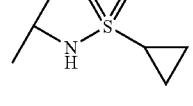 |  |

TABLE 1-continued
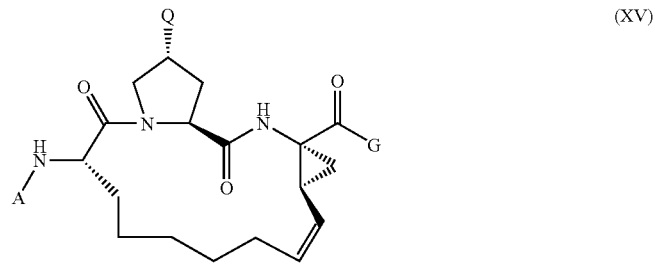
(XV)
| Compound # | A | Q | G |
|---|---|---|---|
| 13 | | | |
| 14 | | | |
| 15 | | | |
| 16 | | | |
| 17 | | | |

TABLE 1-continued (XV)

| Compound # | A | Q | G |
|---|---|---|---|
| 18 | tert-butyl 2-methylpropanoate | 1-naphthylmethoxy | N-cyclopropylsulfonyl |
| 19 | tert-butyl 2-methylpropanoate | 9-anthracenylmethoxy | N-cyclopropylsulfonyl |
| 20 | cyclobutyl 2-methylpropanoate | 2-naphthylmethoxy | N-cyclopropylsulfonyl |
| 21 | cyclopentyl 2-methylpropanoate | 2-naphthylmethoxy | N-cyclopropylsulfonyl |
| 22 | 1-(thiophen-2-yl)propan-1-one | 1-naphthylmethoxy | N-cyclopropylsulfonyl |

TABLE 1-continued
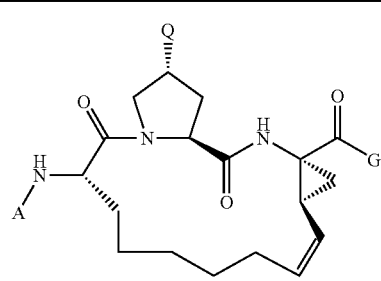
(XV)
| Compound # | A | Q | G |
|---|---|---|---|
| 23 | 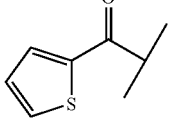 | 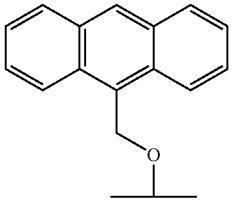 | 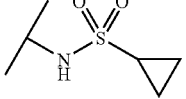 |
| 24 | 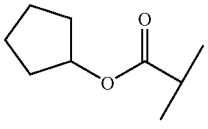 | 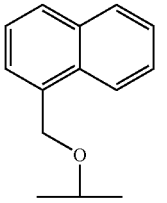 | 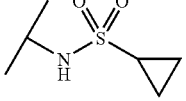 |
| 25 | 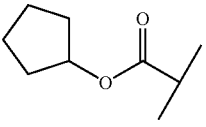 | 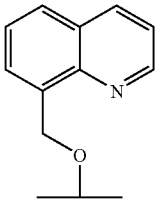 | 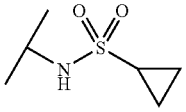 |
| 26 | 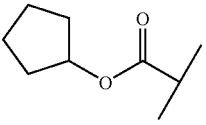 | 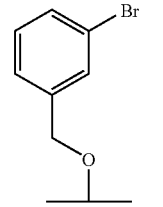 | 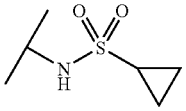 |
| 27 | 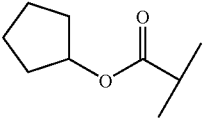 | 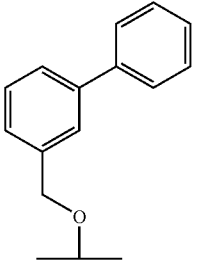 | 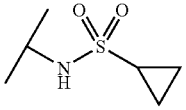 |

TABLE 1-continued
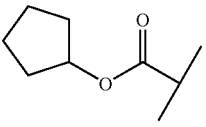
(XV)
| Compound # | A | Q | G |
|---|---|---|---|
| 28 | 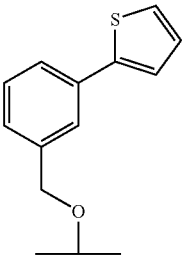 | 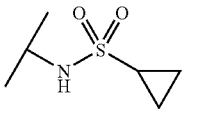 | 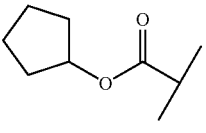 |
| 29 | 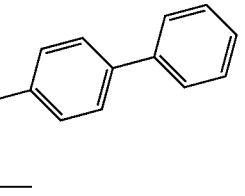 | 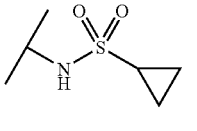 | 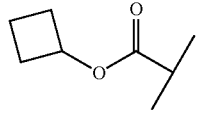 |
| 30 | 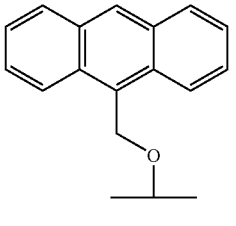 | 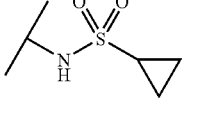 | 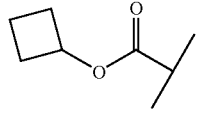 |
| 31 | 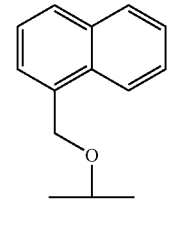 | 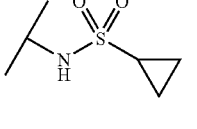 | 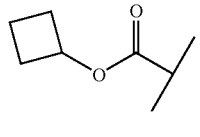 |
| 32 | 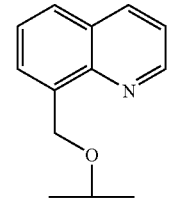 | 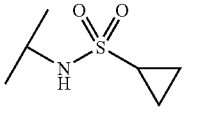 | |

TABLE 1-continued (XV)

| Compound # | A | Q | G |
|---|---|---|---|
| 33 | cyclobutyl ester | 3-bromobenzyloxy | cyclopropylsulfonamide |
| 34 | cyclobutyl ester | 3-phenylbenzyloxy | cyclopropylsulfonamide |
| 35 | cyclobutyl ester | 3-(thiophen-2-yl)benzyloxy | cyclopropylsulfonamide |
| 36 | cyclobutyl ester | 4-phenylbenzyloxy | cyclopropylsulfonamide |

TABLE 1-continued
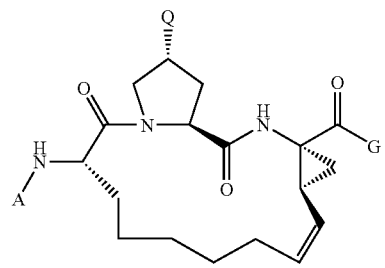
(XV)
| Compound # | A | Q | G |
|---|---|---|---|
| 37 | 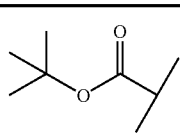 | 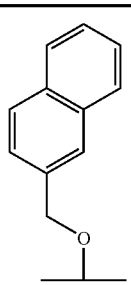 | 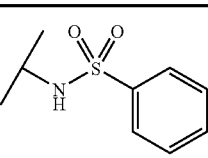 |
| 38 | 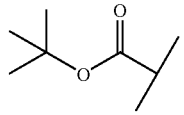 | 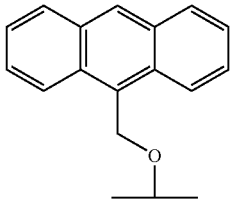 | 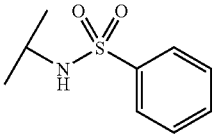 |
| 39 | 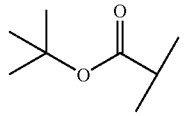 | 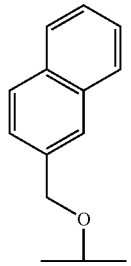 | 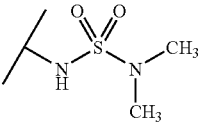 |
| 40 | 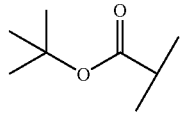 | 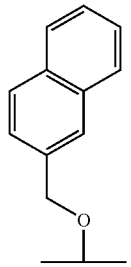 | 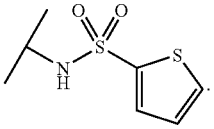 |

7. A compound of claim 1 having the Formula XVI selected from compounds 41-79 of Table 2 wherein A, Q and G are defined in Table 2:
TABLE 2
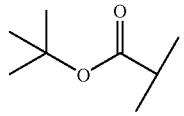
(XVI)
| Compound # | A | Q | G |
|---|---|---|---|
| 41 | 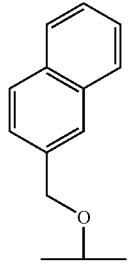 | 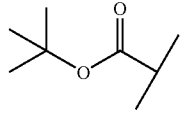 | —OH |
| 42 | 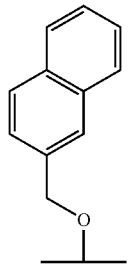 | 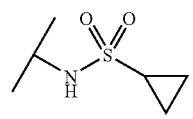 | 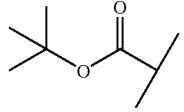 |
| 43 | 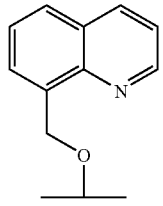 | 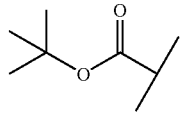 | —OH |
| 44 | 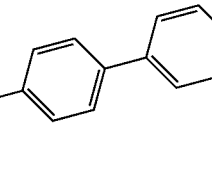 | 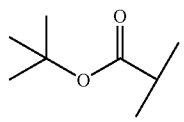 | —OH |
| 45 | 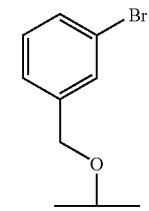 | | —OH |

TABLE 2-continued (XVI)

| Compound # | A | Q | G |
|---|---|---|---|
| 46 | | | —OH |
| 47 | | | —OH |
| 48 | | | —OH |
| 49 | | | —OH |
| 50 | | | —OH |

TABLE 2-continued
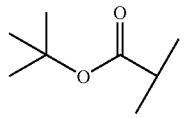
(XVI)
| Compound # | A | Q | G |
|---|---|---|---|
| 51 | 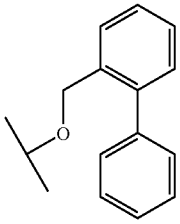 |  | —OH |
| 52 | 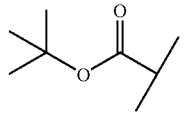 | 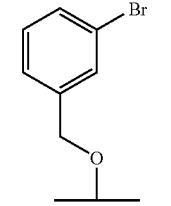 | 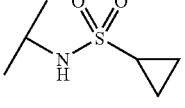 |
| 53 | 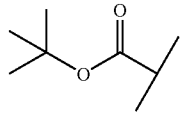 | 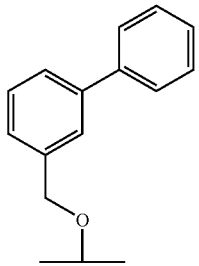 | 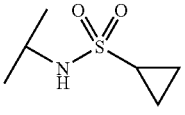 |
| 54 | 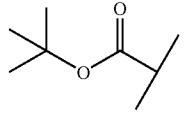 | 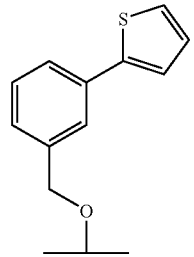 | 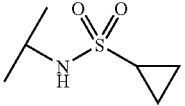 |
| 55 | 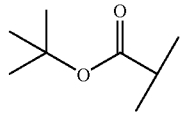 | 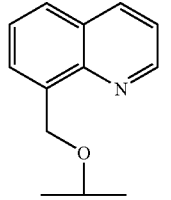 | 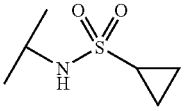 |

TABLE 2-continued (XVI)

| Compound # | A | Q | G |
|---|---|---|---|
| 56 | | | |
| 57 | | | |
| 58 | | | |
| 59 | | | |
| 60 | | | |

TABLE 2-continued (XVI)

| Compound # | A | Q | G |
|---|---|---|---|
| 61 | | | |
| 62 | | | |
| 63 | | | |
| 64 | | | |
| 65 | | | |

TABLE 2-continued (XVI)

| Compound # | A | Q | G |
|---|---|---|---|
| 66 | | | |
| 67 | | | |
| 68 | | | |
| 69 | | | |
| 70 | | | |

TABLE 2-continued (XVI)

| Compound # | A | Q | G |
|---|---|---|---|
| 71 | cyclobutyl-O-C(=O)-CH(CH3)- | quinolin-8-yl-CH2-O- | -C(CH3)(H)-NH-S(=O)2-cyclopropyl |
| 72 | cyclobutyl-O-C(=O)-CH(CH3)- | 3-bromophenyl-CH2-O- | -C(CH3)(H)-NH-S(=O)2-cyclopropyl |
| 73 | cyclobutyl-O-C(=O)-CH(CH3)- | biphenyl-3-yl-CH2-O- | -C(CH3)(H)-NH-S(=O)2-cyclopropyl |
| 74 | cyclobutyl-O-C(=O)-CH(CH3)- | 3-(thiophen-2-yl)phenyl-CH2-O- | -C(CH3)(H)-NH-S(=O)2-cyclopropyl |
| 75 | cyclobutyl-O-C(=O)-CH(CH3)- | biphenyl-4-yl-CH2-O- | -C(CH3)(H)-NH-S(=O)2-cyclopropyl |

TABLE 2-continued
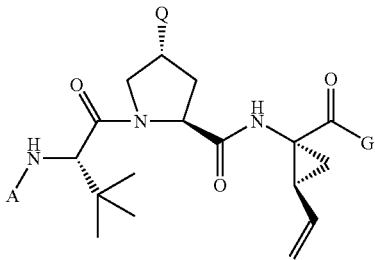

8. A pharmaceutical composition comprising a therapeutically effective amount of a compound according to claim 1 or a pharmaceutically acceptable salt or ester thereof, in combination with a pharmaceutically acceptable carrier or excipient.

9. A pharmaceutical composition comprising a compound of claim 1, or a pharmaceutically acceptable salt or ester thereof.

10. The pharmaceutical composition of claim 9, further comprising another anti-HCV agent.

11. The pharmaceutical composition of claim 9, further comprising an agent selected from interferon, ribavirin, amantadine, another HCV protease inhibitor, an HCV polymerase inhibitor, an HCV helicase inhibitor, or an internal ribosome entry site inhibitor.

12. The pharmaceutical composition of claim 9, farther comprising pegylated interferon.

13. The pharmaceutical composition of claim 9, further comprising another anti-viral, anti-bacterial, anti-fungal or anti-cancer agent, or an immune modulator.

14. A method of treating a hepatitis C viral infection in a subject, comprising administering to the subject a pharmaceutical composition according to claim 8.

15. A method of inhibiting the replication of hepatitis C virus, the method comprising contacting the hepatitis C virus with a compound of claim 1.

16. A method of claim 14 further comprising administering an additional anti-hepatitis C virus agent.

17. The method of claim 16, wherein said additional anti-hepatitis C virus agent is selected from the group consisting of α-interferon, β-interferon, ribavarin, and adamantine.

18. The method of claim 16, wherein said additional anti-hepatitis C virus agent is an inhibitor of other targets in the hepatitis C virus life cycle which is selected from the group consisting of helicase, polymerase, metalloprotease, and IRES.

* * * * *

UNITED STATES PATENT AND TRADEMARK OFFICE
CERTIFICATE OF CORRECTION

| | | |
|---|---|---|
| PATENT NO. | : 7,687,459 B2 | Page 1 of 1 |
| APPLICATION NO. | : 11/836288 | |
| DATED | : March 30, 2010 | |
| INVENTOR(S) | : Deqiang Niu et al. | |

It is certified that error appears in the above-identified patent and that said Letters Patent is hereby corrected as shown below:

Column 98, Claim 1, line 36, after "from" delete "0" and replace with --O--;
Column 98, Claim 1, line 37, delete "5" and replace with --S--;

Column 99, Claim 1, line 11, after "from" delete "0, 5" and replace with --O, S--;
Column 99, Claim 1, line 32, delete "alkynyl" and replace with --alkenyl--;
Column 99, Claim 1, line 49, after "from O," insert --S--;
Column 99, Claim 1, line 54, after "from O," insert --S--;
Column 99, Claim 1, line 58, after "from O," insert --S--;

Column 104, Claim 5, line 38, after "CH2NR4" delete "R5";

Column 137, Claim 12, line 16, delete "farther" and replace with --further--.

Signed and Sealed this

Thirty-first Day of August, 2010

David J. Kappos
*Director of the United States Patent and Trademark Office*